US011627937B2

(12) United States Patent
Barbic et al.

(10) Patent No.: US 11,627,937 B2
(45) Date of Patent: Apr. 18, 2023

(54) POSITIONING APPARATUS AND GRIPPING APPARATUS

(71) Applicant: Howard Hughes Medical Institute, Chevy Chase, MD (US)

(72) Inventors: Mladen Barbic, Sterling, VA (US); Richard Smith, Pasadena, CA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 0 days.

(21) Appl. No.: 17/895,546

(22) Filed: Aug. 25, 2022

(65) Prior Publication Data
US 2022/0401065 A1      Dec. 22, 2022

Related U.S. Application Data

(62) Division of application No. 16/538,281, filed on Aug. 12, 2019, now Pat. No. 11,471,125.

(Continued)

(51) Int. Cl.
*A61B 8/00* (2006.01)
*B01L 9/00* (2006.01)
*B01L 9/06* (2006.01)

(52) U.S. Cl.
CPC ............ *A61B 8/4209* (2013.01); *A61B 8/546* (2013.01); *B01L 9/50* (2013.01);
(Continued)

(58) Field of Classification Search
CPC .................. A61B 8/4209; A61B 8/546; A61B 2560/0242; A61B 2560/0462;
(Continued)

(56) References Cited

U.S. PATENT DOCUMENTS

| 5,928,143 A | 7/1999 | McNaughton |
| 2012/0279812 A1 | 11/2012 | Peters et al. |

FOREIGN PATENT DOCUMENTS

| JP | 2007-174770 A | 7/2007 |
| JP | 5067487 B2 | 11/2012 |

OTHER PUBLICATIONS

Inchworm motor—Wikipedia, https://en.wikipedia/wiki/Inchworm_motor (as of May 20, 2014, 18:16 GMT), 2 pages.
(Continued)

*Primary Examiner* — Brandi N Hopkins
(74) *Attorney, Agent, or Firm* — DiBerardino McGovern IP Group LLC

(57) ABSTRACT

A gripping apparatus includes: a temperature adjusting device held in a substrate wherein the substrate defines an open region; a phase change material held within the open region and thermally coupled with the temperature adjusting device such that a temperature change in the temperature adjusting device causes a temperature change in the phase change material; and a controller connected to the temperature adjusting device and configured to send a signal to the temperature adjusting device to change its temperature and thereby change the temperature of the phase change material that is thermally coupled with the temperature adjusting device. The phase change material is either in a solid state and configured to grip a stick or in a liquid state and the phase change material and configured to loosen its grip on the stick such that the stick is capable of moving through the phase change material.

29 Claims, 21 Drawing Sheets

Related U.S. Application Data

(60) Provisional application No. 62/718,251, filed on Aug. 13, 2018.

(52) U.S. Cl.
CPC ............... *A61B 2560/0242* (2013.01); *A61B 2560/0462* (2013.01); *A61B 2560/063* (2013.01)

(58) Field of Classification Search
CPC ....... A61B 2560/063; B01L 9/50; B01L 9/06; G01L 5/0033; F03G 7/065; A63F 13/22; G01N 3/18; G01N 3/54; B23Q 17/005; B23Q 17/0923; H01L 24/743; A61C 13/0028; B25J 19/0054; B25J 15/12; B21D 26/041; H02N 2/021; H02N 2/008; H02N 2/00; B60K 28/06; F21V 14/02; E21B 41/00; B23B 31/207
See application file for complete search history.

(56) References Cited

OTHER PUBLICATIONS

Sindhu Anand et al., "Electrothermal Microactuators With Peg Drive Improve Performance for Brain Implant Applications," J. Microelectromech. Sys., vol. 21, No. 5, 1172-86 (Oct. 2012).
Mladen Barbie et al., "Detachable glass microelectrodes for recording action potentials in active moving organs," Am. J. Physiol. Heart Circ. Physiol., vol. 312, H1248-59, doi:10.1152/ajpheart.00741. 2016 (2017).
Francesco Battaglia et al., "The Lantern: An ultra-light micro-drive for multi-tetrode recordings in mice and other small animals," J. Neurosci. Methods, vol. 178, 291-300, doi:10.1016/j.jneuMethods2008. 12.024 (2009).
Jorge G. Cham et al., "Semi-Chronic Motorized Microdrive and Control Algorithm for Autonomously Isolating and Maintaining Optimal Extracellular Action Potentials," J. Neurophysiol., vol. 93, 570-79 (2005).
Richard Eckhom and Uwe Thomas, "A new method for the insertion of multiple microprobes into neural and muscular tissue, including fiber electrodes, fine wires, needles and microsensors," J. Neurosci. Methods, vol. 49, 175-79 (1993).
Michale S. Fee and Anthony Leonardo, "Miniature motorized microdrive and commutator system for chronic neural recording in small animals," J. Neurosci. Methods, vol. 112, 83-94 (2001).
F. Orlando Galashan et al., "A new type of recording chamber with an easy-to-exchange microdrive array for chronic recordings in macaque monkeys," J. Neurophysiol., vol. 105, 3092-105, doi:10. 1152/jn.00508.2010 (2011).
Charles M. Gray et al., "Multichannel Micromanipulator and Chamber System for Recording Multineuronal Activity in Alert, Non-Human Primates," J. Neurophysiol., vol. 98, 527-36 (2007).
Florent Haiss et al., "A miniaturized chronic microelectrode drive for awake behaving head restrained mice and rats," J. Neurosci. Methods, vol. 187, 67-72, doi:10.1016/j.jneuMethods2009.12.015 (2010).
Donald R. Humphrey, "A chronically implantable multiple microelectrode system with independent control of electrode positions," Electroencephalogr. Clin. Neurophysiol., vol. 29, 616-20 (1970).
Andrew Jackson and Eberhard Fetz, "Compact Movable Microwire Array for Long-Term Chronic Unit Recording in Cerebral Cortex of Primates," J. Neurophysiol., vol. 98, 3109-18 (2007).
Nathan Jackson et al., "Long-term neural recordings using MEMS based movable microelectrodes in the brain/" Front. Neuroeng., vol. 3, Article 10, 1-11, doi:10.3389/fneng.2010.00010 (2010).
Yannick Jeantet and Yoon Cho, "Design of a twin tetrode microdrive and headstage for hippocampal single unit recordings in behaving mice," J. Neurosci. Methods, vol. 129, 129-34 (2003).

M.S. Jog et al., "Tetrode technology: advances in implantable hardware, neuroimaging, and data analysis techniques," J. Neurosci. Methods, vol. 117, 141-52 (2002).
Jennie Johnson and John Welsh, "Independently movable multielectrode array to record multiple fast-spiking neurons in the cerebral cortex during cognition." Methods, vol. 30, 64-78 (2003).
Victor Korshunov, "Miniature microdrive-headstage assembly for extracellular recording of neuronal activity with high-impedance electrodes in freely moving mice," J. Neurosci. Methods, vol. 158, 179-85, doi:10.1016/j.ineuMethods2006.05.031 (2006).
John Kubie, "A Driveable Bundle of Microwires for Collecting Single-Unit Data from Freely-Moving Rats," Physiol. Behav., vol. 32, 115-18 (1984).
Carien S. Lansink et al.. "A split microdrive for simultaneous multi-electrode recordings from two brain areas in awake small animals," J. Neurosci. Methods, vol. 162, 129-38, doi:10.1016/j. jneuMethods2006.12.016 (2007).
Li Liang et al., "Scalable, Lightweight, Integrated and Quick-to-Assemble (SLIQ) Hyperdrives for Functional Circuit Dissection," Front. Neural Circuits vol. 11, Article 8, 1-11, doi: 10.3389/fncir. 2017.00008 (2017).
Teppei Matsui et al., "MRI-based localization of electrophysiological recording sites within the cerebral cortex at single-voxel accuracy," Nat. Methods, vol. 4, No. 2, 161-68 (2007).
Bradley Nelson et al., "Microrobots for Minimally Invasive Medicine," Annu. Rev. Biomed. Eng., vol. 12, 55-85 (2010).
Altah M. Nichols et al., "A screw microdrive for adjustable chronic unit recording in monkeys," J. Neurosci. Methods, vol. 81, 185-88 (1998).
Sangkyu Park et al., "The development of a PZT-based microdrive for neural signal recording," Smart Mater. Struct., vol. 17, 1-7, doi: 10.1088/0964-1726/17/2/027001 (2008).
Herbert J.P. Reitboeck, A 19-Channel Matrix Drive with Individually Controllable Fiber Microelectrodes for Neurophysiological Applications,: IEEE Trans. Sys. Man. Cybernetics, vol. SMC-13, No. 5, 676-83 (1983).
T. Sato et al., "A new multi-electrode array design for chronic neural recording, with independent and automatic hydraulic positioning," J Neurosci. Methods, vol. 160, 45-51 (2007).
Harvey A. Swadlow et al., "A Multi-Channel, Implantable Microdrive System for Use with Sharp, Ultra-Fine "Reitboeck" Microelectrodes, "J. Neurophysiol., vol. 93, 2959-65, doi:10.1152/jn.01141.2004 (2005).
Yaroslav Sych et al., "High-density multi-fiber photometry for studying large-scale brain circuit dynamics," Nat. Methods, vol. 16, 553-60, doi:10.1038/s41592-019-0400-4 (2019).
Imre Szabo et al., "The application of printed circuit board technology for fabrication of multi-channel micro-drives," J. Neurosci. Methods, vol. 105, 105-10 (2001).
Attila Toth et al., "Improved version of the printed circuit board (PCB) modular multi-channel microdrive for extracellular electrophysiological recordings," J. Neurosci. Methods, vol. 159, 51-56, doi:10. 1016/j.jneuMethods2006.06.014 (2007).
Suri Venkatachalam et al., "Ultra-miniature headstage with 6-channel drive and vacuum-assisted micro-wire implantation for chronic recording from the neocortex," J. Neurosci Methods, vol. 90, 37-46 (1999).
Jakob Voigts et al., "The flexDrive: an ultra-light implant for optical control and highly parallel chronic recording of neuronal ensembles in freely moving mice," Front. Sys. Neurosci., vol. 7, Article 8, 1-9, doi: 10.3389/fnsys.2013.00008 (2013).
Fraser Wilson et al., "A microelectrode drive for long term recording of neurons in freely moving and chaired monkeys," J. Neurosci. Methods, vol. 127, 49-61 (2002).
Jun Yamamoto and Matthew A. Wilson, "Large-Scale Chronically Implantable Precision Motorized Microdrive Array for Freely Behaving Animals," J. Neurophysiol., vol. 100, 2430-40 (2008).
Sungwook Yang et al., "Piezo motor based Microdrive for Neural Signal Recording," 30th Annu. Int"l IEEE EMBS Conf., Vancouver, BC, Canada, Aug. 20-24, 2008, 3364-67 (2008).
Sungwook Yang et al., "Feedback controlled piezo-motor microdrive for accurate electrode positioning in chronic single unit recording in

(56) References Cited

OTHER PUBLICATIONS behaving mice," J. Neurosci. Methods, vol. 195, 117-27, doi:10.1016/j.jneuMethods2010.09.006 (2011).

Rachel S. Zoll et al., "MEMS-Actuated Carbon Fiber Microelectrode for Neural Recording," IEEE Trans. Nanobiosci., vol. 18, No. 2, 234-39 (2019).

Santosh Devasia et al., "A Survey of Control Issues in Nanopositioning," IEE Trans. Control Sys. Technol., vol. 15, No. 5, 802-23 (2007).

Jeff G. Keating and George L. Gerstein, "A chronic multi-electrode microdrive for small animals," J. Neurosci. Methods, vol. 117, 201-06 (2002).

Suhasa B. Kodandaramaiah et al. "Automated whole-cell patch-clamp electrophysiology of neurons in vivo," Nat. Methods, vol. 9, 585-87, doi:10.1038/nmeth.1993 (2012).

Suhasa B. Kodandaramaiah et al., "Multi-neuron intracellular recording in vivo via interacting autopatching robots," eLlife, 7:e24656, 1-19, doi:10.7554/eLife.24656 (2018).

V.A. Korshunov, "Miniature microdrive for extracellular recording of neuronal activity in freely moving animals," J. Neurosci. Methods, vol. 57, 77-80 (1995).

Jurgen Kruger, "Simultaneous Individual Recordings From Many Cerebral Neurons: Techniques and Results," Rev. Physiol. Biochem Pharmacol, vol. 98, 177-233 (1983).

P. R. Ouyang et al., "Micro-motion devices technology: The state of arts review," Int. J. Adv. Manuf. Technol., vol. 38, 463-78 (2007).

Paras R. Patel et al., "Insertion of linear 8.4pm diameter 16 channel carbon fiber electrode arrays for single unit recordings," J. Neural Eng., vol. 12, 046009, doi:10.1088/1741-2560/12/4/046009 (2015).

Lucas Santos et al., "A novel tetrode microdrive for simultaneous multi-neuron recording from different regions of primate brain," J. Neurosci. Methods, vol. 205, 368-74 (2012).

R. Venkateswaran et al., "A Motorized Microdrive for Recording of Neural Ensembles in Awake Behaving Rats," J. Biomech. Eng , vol. 127, 1035-40 (2005).

Bart P. Vos et al., "Miniature carrier with six independently moveable electrodes for recording of multiple single-units in the cerebellar cortex of awake rats," J. Neurosci. Methods, vol. 94, 19-26 (1999).

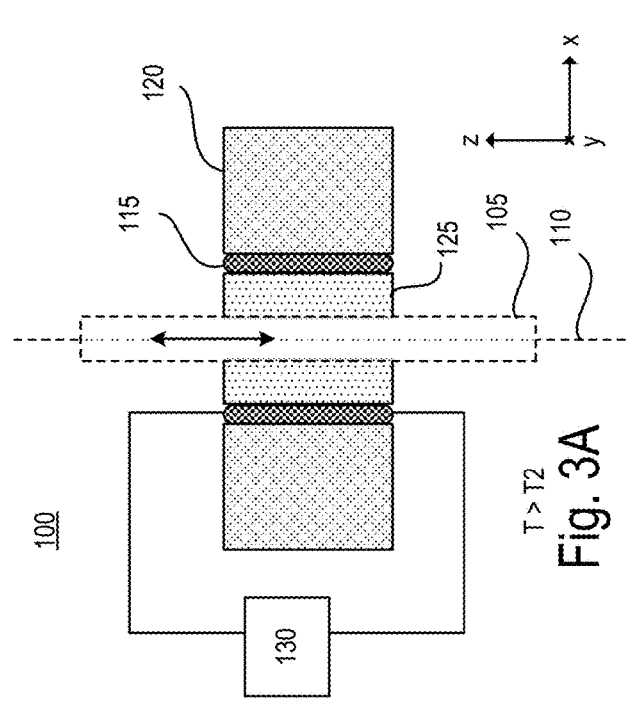
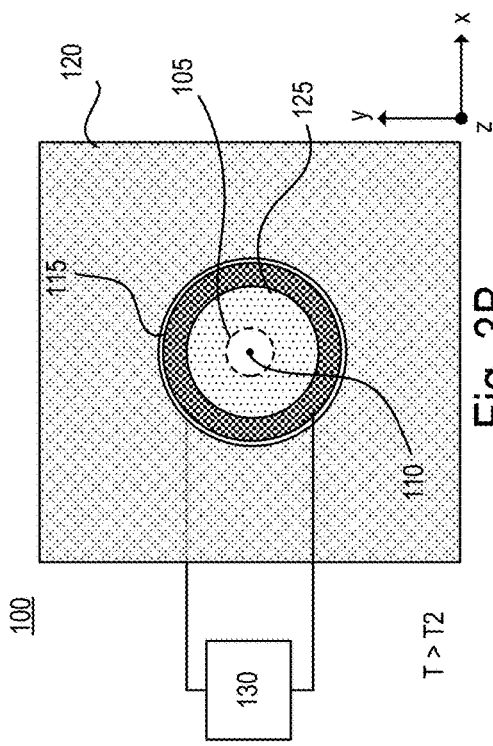
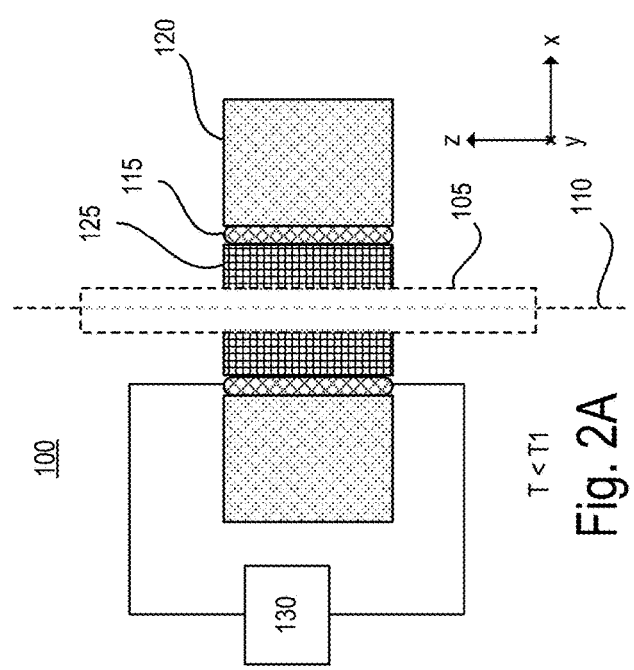
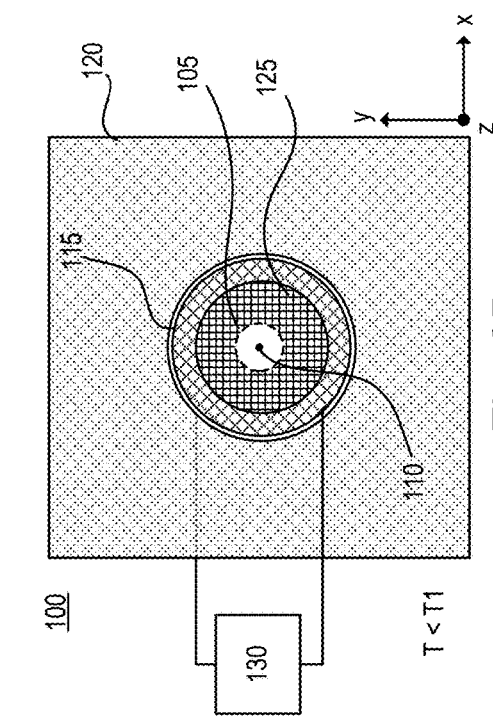

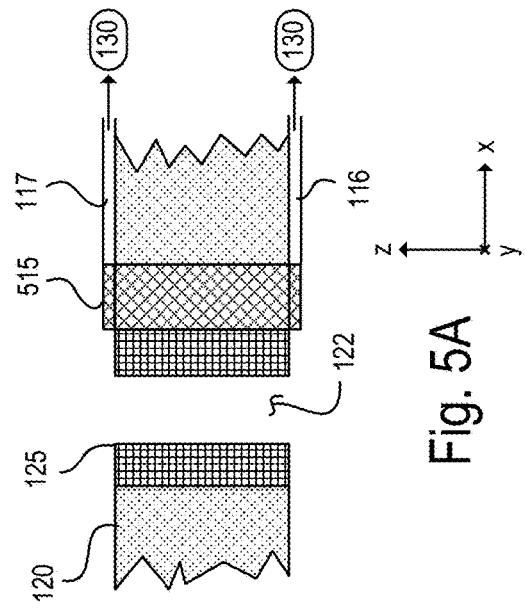
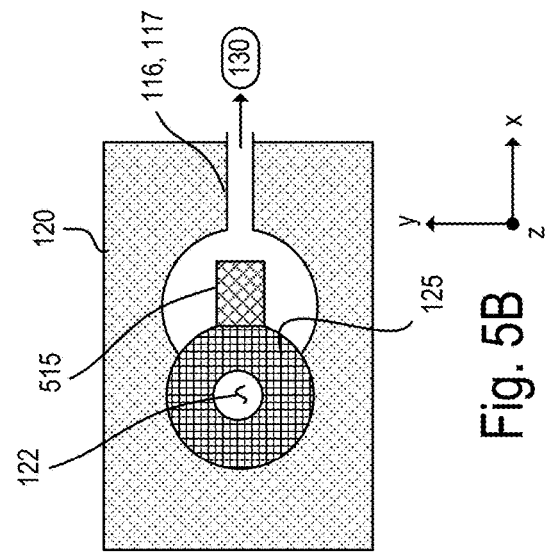
Fig. 4A
Fig. 5A
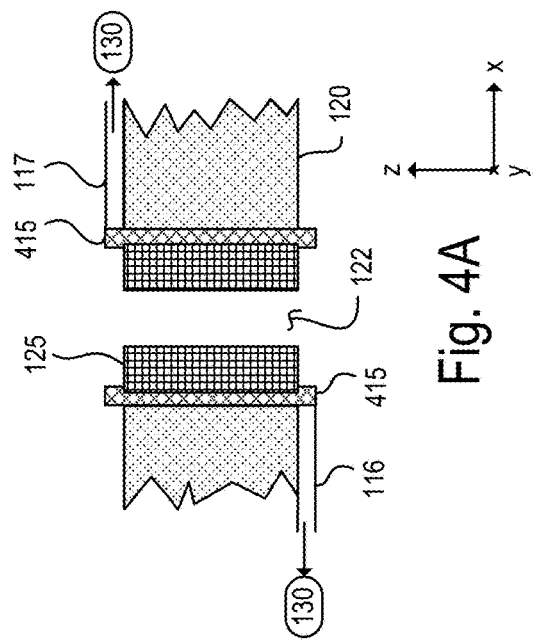
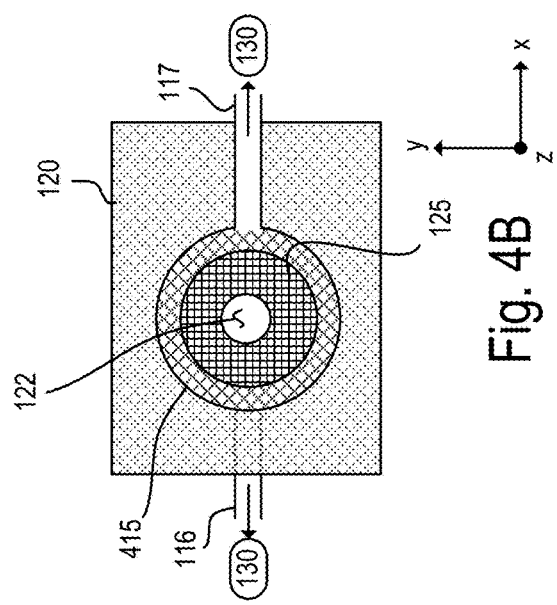
Fig. 4B
Fig. 5B

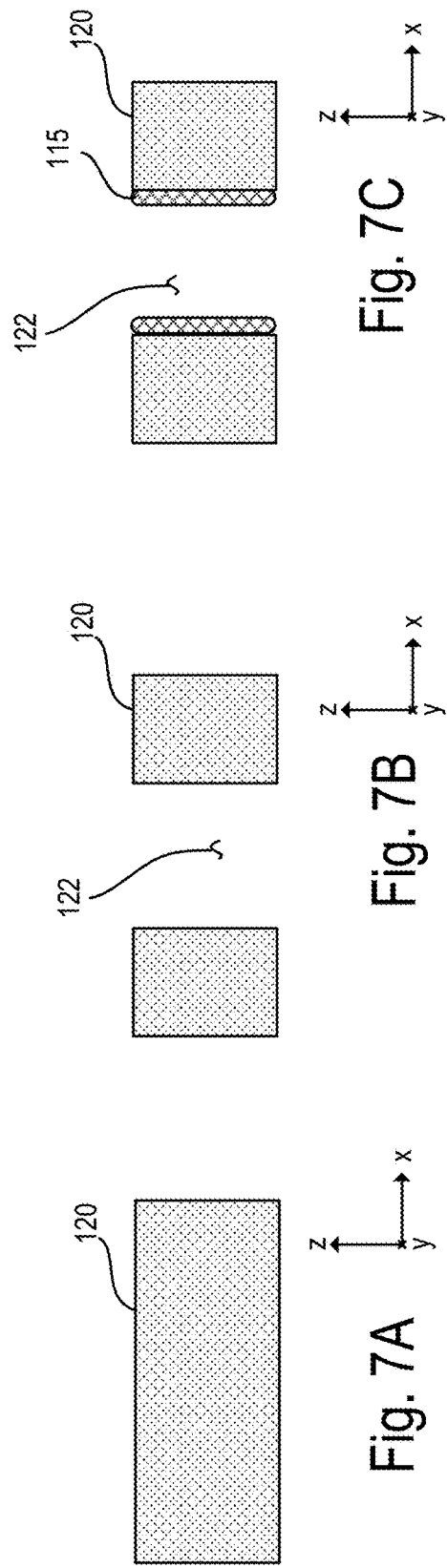
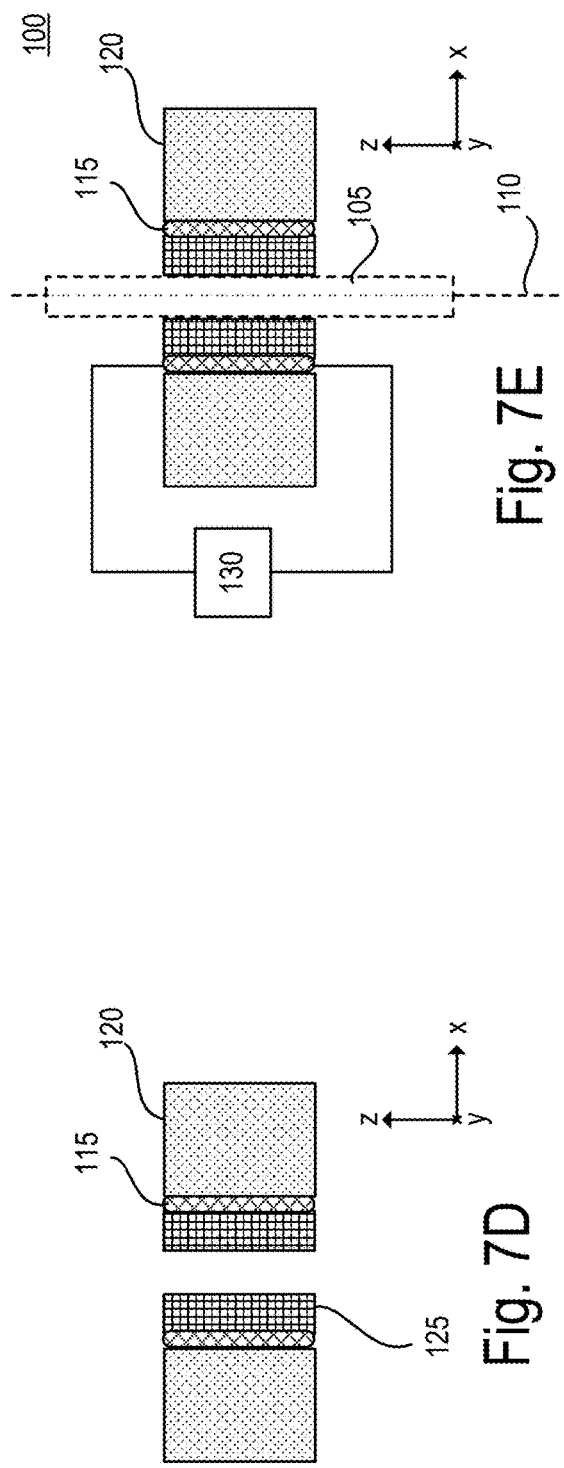

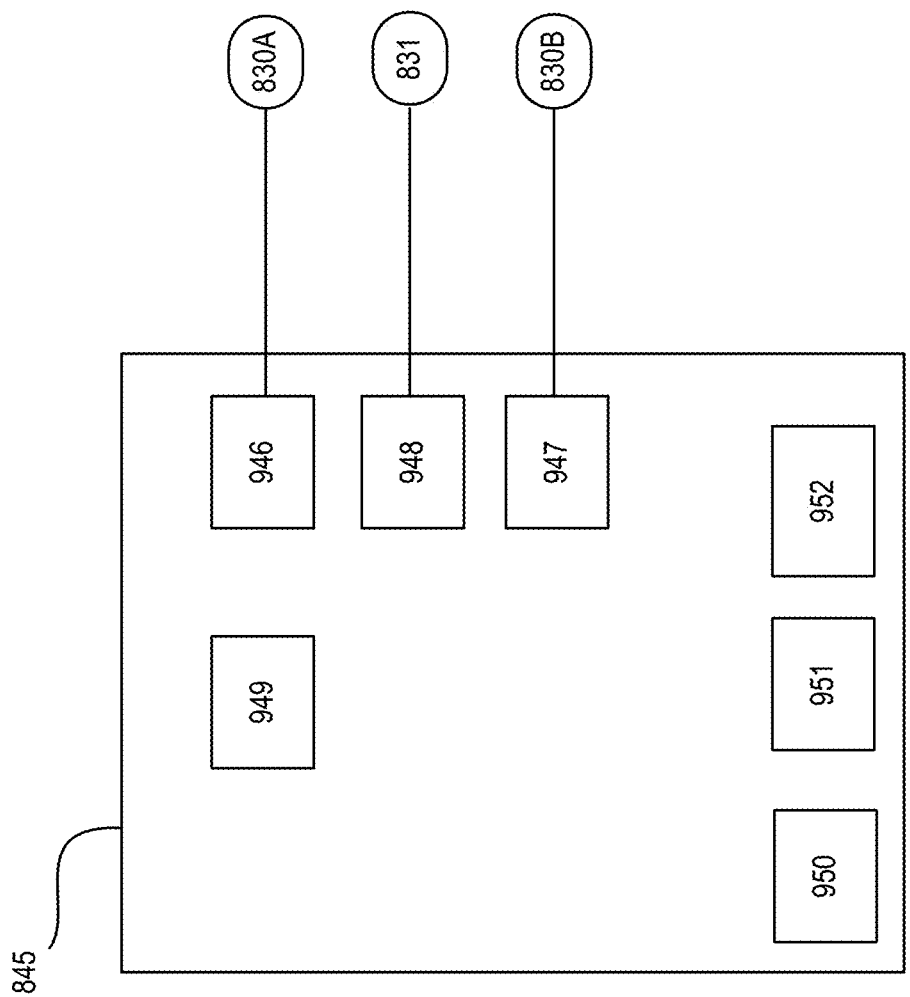

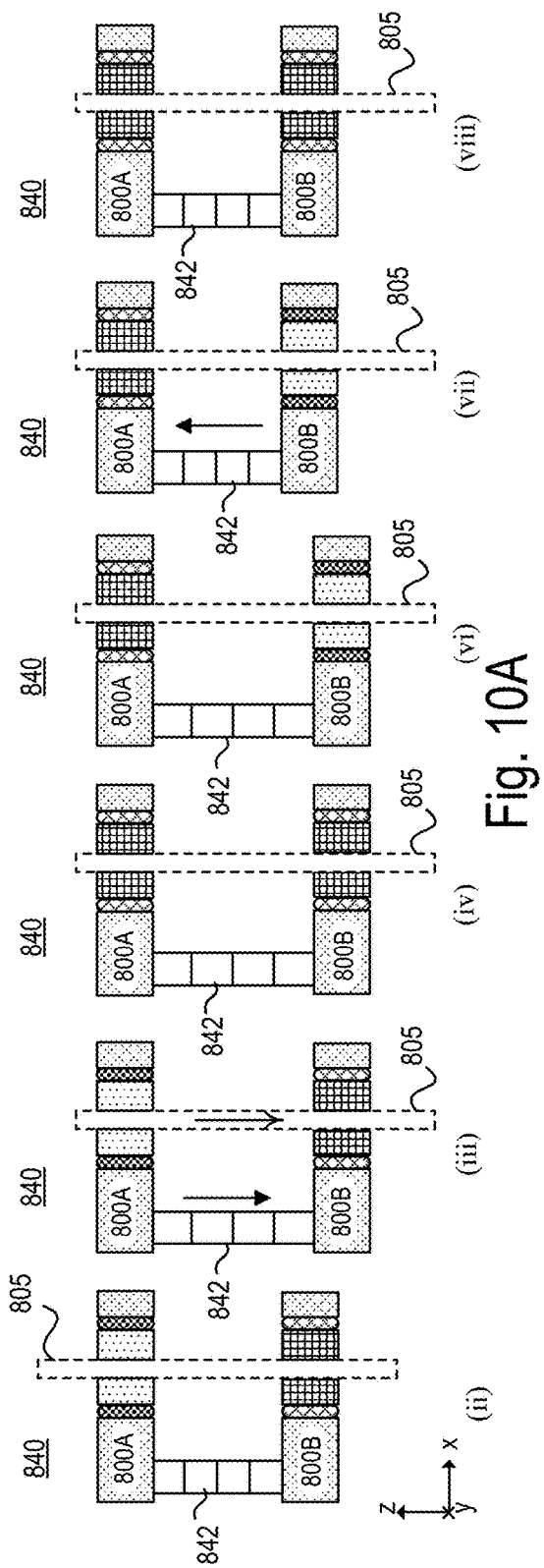
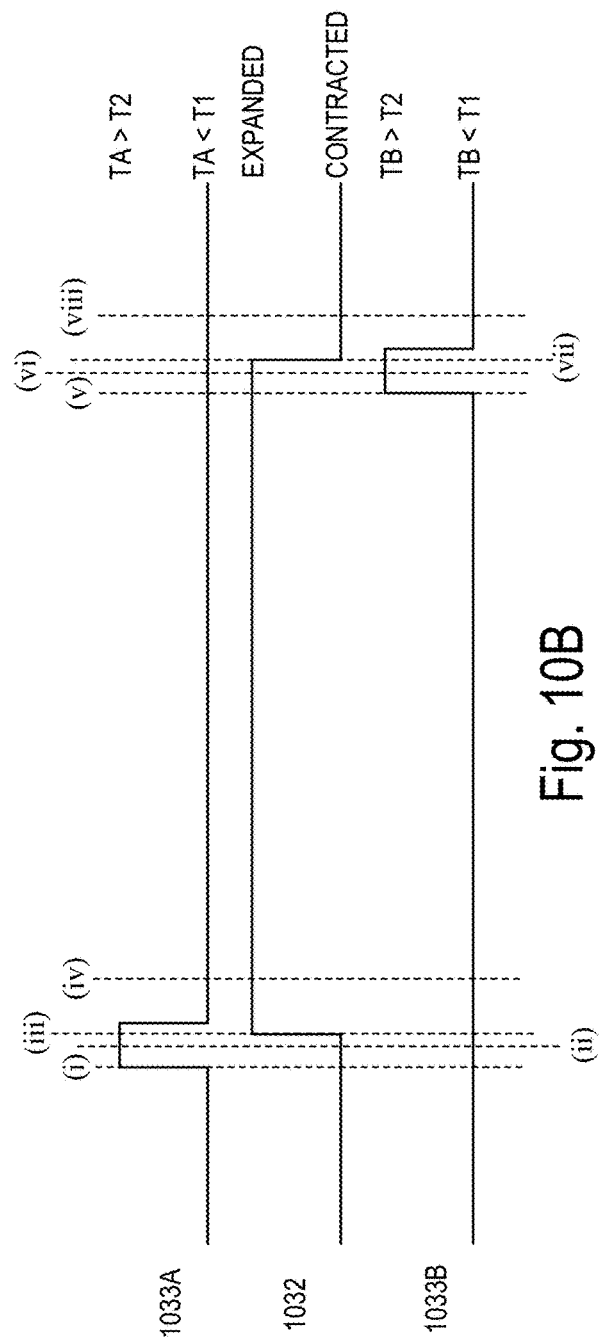
Fig. 10A
Fig. 10B

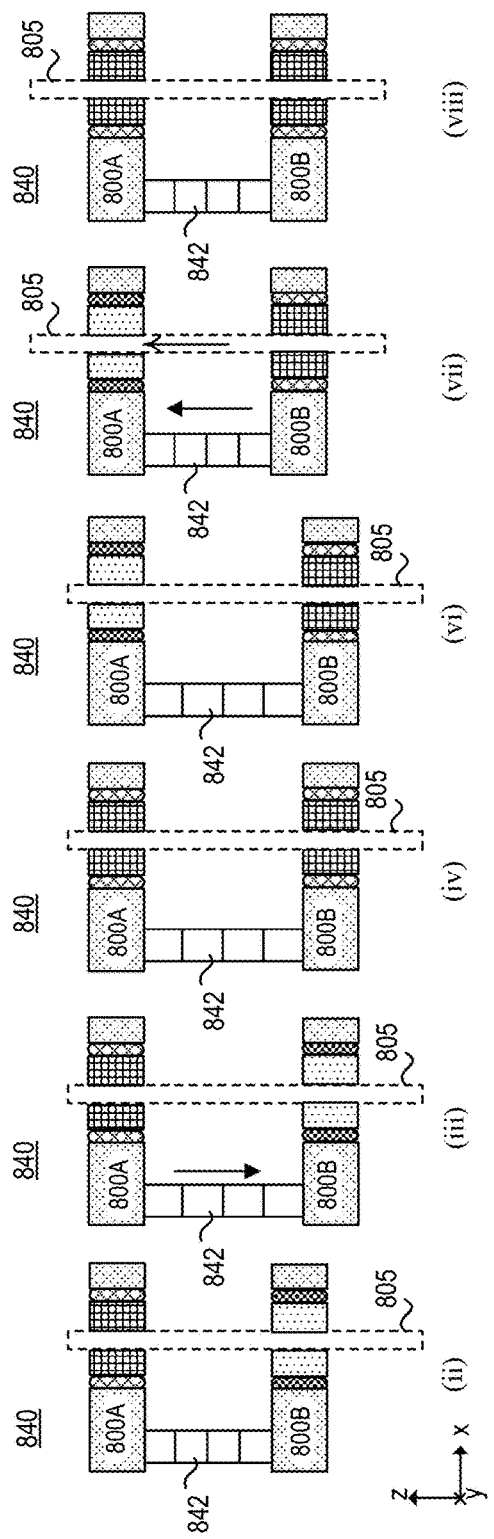
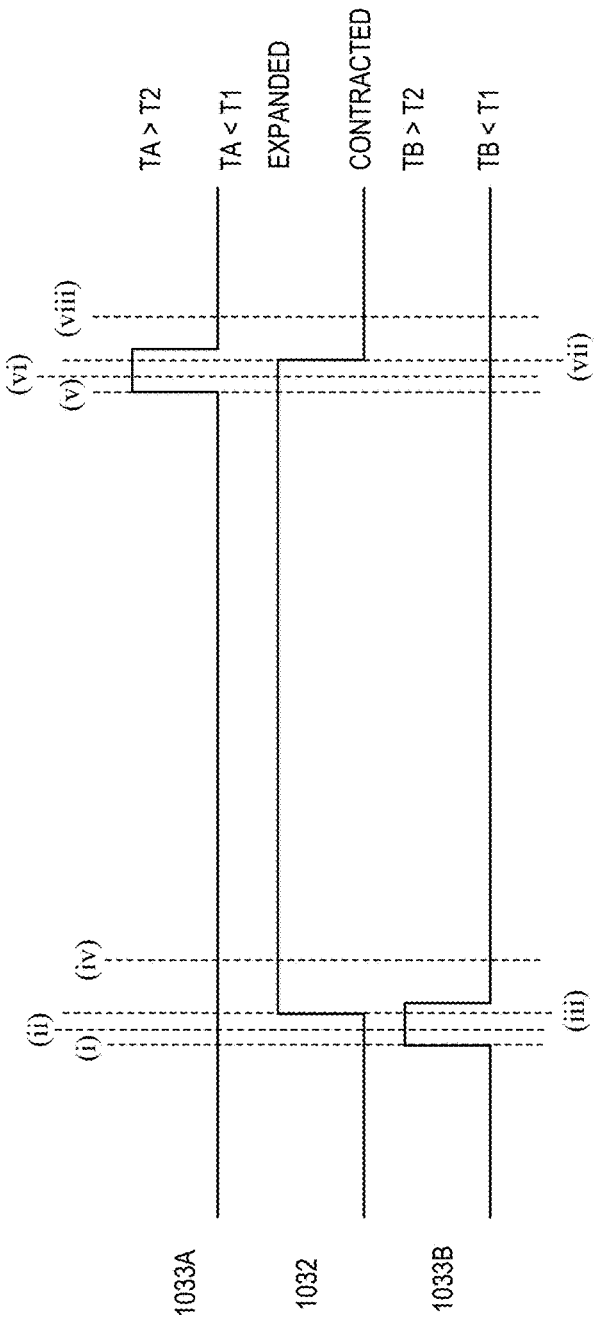
Fig. 11A
Fig. 11B

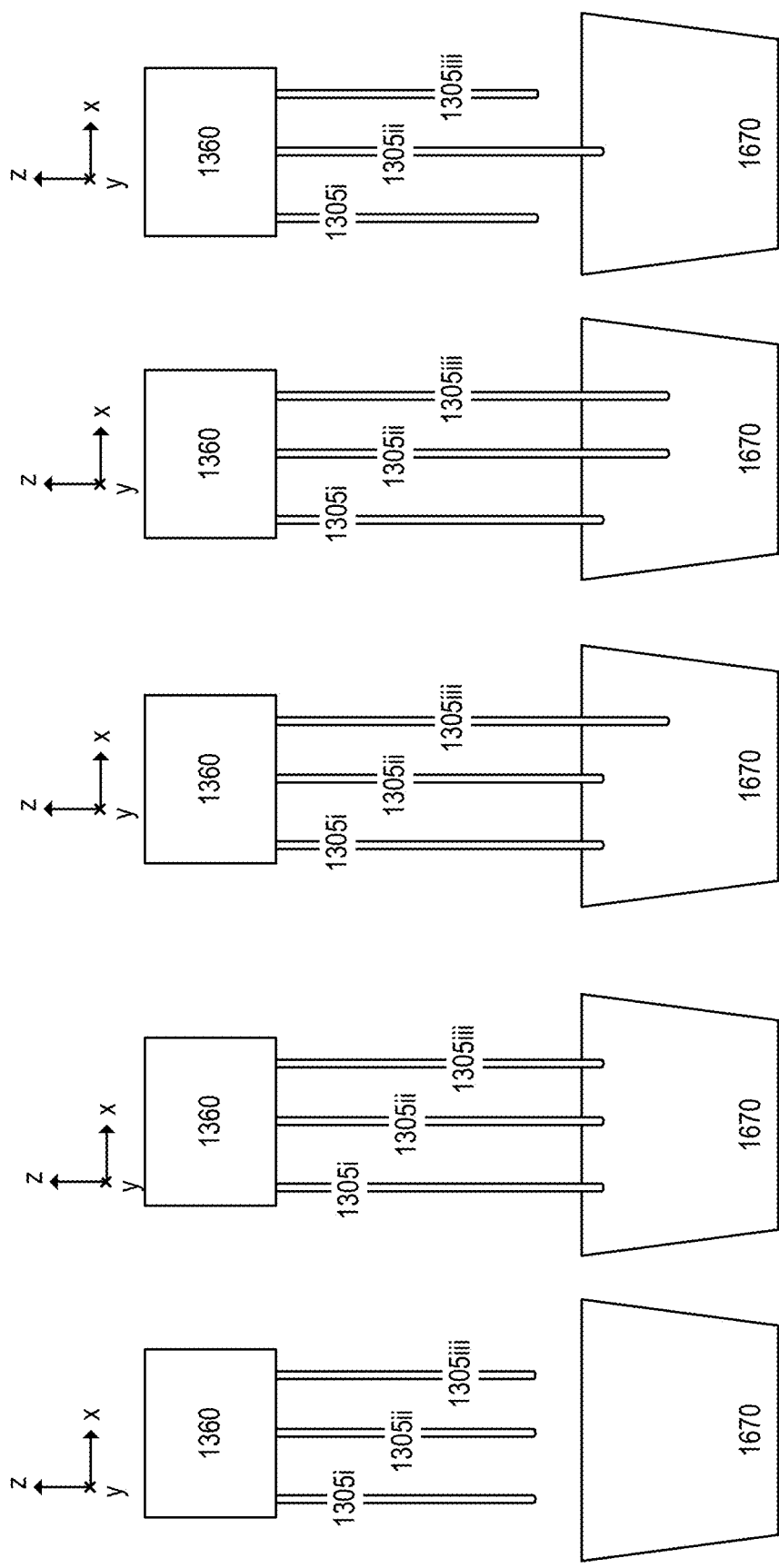

POSITIONING APPARATUS AND GRIPPING APPARATUS

CROSS REFERENCE TO RELATED APPLICATION

This application is a divisional of U.S. application Ser. No. 16/538,281, filed on Aug. 12, 2019 and titled POSITIONING APPARATUS AND GRIPPING APPARATUS, which claims the benefit of U.S. Application No. 62/718,251, filed Aug. 13, 2018 and titled POSITIONING APPARATUS AND GRIPPING APPARATUS. Both of these applications are incorporated herein by reference in their entirety.

TECHNICAL FIELD

This disclosure relates to a gripping apparatus configured to control a grip on and a motion of a stick and a positioning apparatus in which the gripping apparatus can be used.

BACKGROUND

Probes can be used to research animal tissue, for example, for neurophysiological research or for clinical diagnostic uses in animals. For example, a movable single channel or single electrode mechanism can record from a single location (such as a visual cortex) in the brain of an animal.

SUMMARY

In some general aspects, a gripping apparatus includes: a temperature adjusting device held in a substrate wherein the substrate defines an open region; a phase change material held within the open region and thermally coupled with the temperature adjusting device such that a temperature change in the temperature adjusting device causes a temperature change in the phase change material; and a controller connected to the temperature adjusting device and configured to send a signal to the temperature adjusting device to change its temperature and thereby change the temperature of the phase change material that is thermally coupled with the temperature adjusting device. When the phase change material is at a temperature below a first transition temperature, the phase change material is in a solid state and the phase change material is configured to grip a stick within the phase change material. When the phase change material is at a temperature above a second transition temperature, the phase change material is in a liquid state and the phase change material is configured to loosen its grip on the stick such that the stick is capable of moving through the phase change material.

Implementations can include one or more of the following features. For example, the stick can extend through the phase change material.

The phase change material can include one or more of: wax; paraffin wax; and alkane hydrocarbon. The alkane hydrocarbon can include one or more of: n-octacosane, n-heptacosane, n-hexacosane, n-pentacosane, n-tetracosane, n-docosane, n-tricosane, n-heneicosane, n-eicosane, n-nonadecane, n-octadecane, n-heptadecane, n-hexadecane, n-pentadecane, n-tetradecane, and n-tridecane. The phase change material can be selected so that the transition between the solid state and the liquid state at the first or second transition temperature occurs at an operating temperature for the gripping apparatus.

The stick can be rigid enough to withstand motion through the phase change material without fracturing or bending or kinking.

The first transition temperature and the second transition temperature can be at room temperature, at a temperature of a living organism, at a temperature below room temperature, or at a temperature above room temperature.

The stick can include one or more of: at least one conductor; at least one measurement probe; at least one capillary tube; at least one optical waveguide; and at least one carbon fiber; and at least one sonic waveguide. The at least one measurement probe can include an electrical testing probe, a silicon probe, an electrical recording probe, or an ultrasonic probe.

The substrate can generally be defined in an x-y plane, and when the phase change material can be at a temperature above the second transition temperature, the stick being capable of moving through the phase change material along a z axis that is perpendicular to the x-y plane.

A cross section of the stick taken along a plane can be a circular shape, a polygonal shape, or an irregular asymmetric shape.

The temperature adjusting device can include a resistive conductive wire and the controller can include a power source that supplies a current to the resistive conductive wire, wherein the resistive conductive wire changes its temperature as the current is changed. The temperature adjusting device can include one or more of: a resistive material deposited in the open region of the substrate; a chip resistor adjacent to the open region of the substrate; a wire-wound resistor in the open region of the substrate; and a carbon paste coated in the open region of the substrate.

The substrate can include a printed circuit board.

The phase change material can be held within the open region by way of capillary forces. The phase change material can remain within the open region even if it is in the liquid state.

The first transition temperature can be equal to the second transition temperature.

In other general aspects, a positioning apparatus includes: an actuator drive movable along an axial direction; a first gripping apparatus fixed to the actuator drive, the first gripping apparatus including a first phase change material that is configured to receive a first region of a stick; a second gripping apparatus fixed to the actuator drive, the second gripping apparatus including a second phase change material that is aligned along an axial direction with the first phase change material and that is configured to receive a second region of the stick; and a controller connected to the first gripping apparatus, the second gripping apparatus, and to the actuator drive. The controller is configured to provide one or more signals to the actuator drive, the first gripping apparatus, and the second gripping apparatus. The one or more signals provided to the first gripping apparatus control a phase of the first phase change material and the one or more signals provided to the second gripping apparatus control a phase of the second phase change material. A position of the stick along the axial direction is adjusted or held constant depending on the one or more signals provided to the actuator drive, the first gripping apparatus, and the second gripping apparatus.

Implementations can include one or more of the following features. For example, the actuator drive can have a first end and a second end. The first and second ends can be movable relative to each other. The first gripping apparatus can be fixed to the first end of the actuator drive. The second gripping apparatus can be fixed to the second end of the actuator drive.

The actuator drive can include one or more of: a turnable screw configured to turn about the axial direction to thereby translate the second end relative to the first end along the axial direction; a stepper motor configured to move the second end relative to the first end along the axial direction; a shape memory alloy configured to expand or contract to thereby adjust a relative position between the first end and the second end; and a piezoelectric actuator configured to move the second end relative to the first end along the axial direction.

The first end of the actuator drive can be fixed and the second end of the actuator drive can be movable relative to the first end of the actuator drive.

The actuator drive can be movable along only the axial direction under control of the controller. The first gripping apparatus can further include: a first temperature adjusting device held in a first rigid substrate, the first rigid substrate defining a first open region and being fixed to the actuator drive to thereby fix the first gripping apparatus to the actuator drive. The first phase change material can be held within the first open region and can be thermally coupled with the first temperature adjusting device such that a temperature change in the first temperature adjusting device causes a temperature change in the first phase change material. The controller can be connected to the first temperature adjusting device of the first gripping apparatus such that the provision of the signal to the first gripping apparatus controls a temperature of the first temperature adjusting device to thereby control a temperature of the first phase change material. The second gripping apparatus can further include: a second temperature adjusting device held in a second rigid substrate, the second rigid substrate defining a second open region and being fixed to the actuator drive to thereby fix the second gripping apparatus to the actuator drive. The second phase change material can be held within the second open region and can be thermally coupled with the second temperature adjusting device such that a temperature change in the second temperature adjusting device causes a temperature change in the second phase change material. The controller can be connected to the second temperature adjusting device of the second gripping apparatus such that the provision of the signal to the second gripping apparatus controls a temperature of the second temperature adjusting device to thereby control a temperature of the second phase change material.

The controller can include: a first control module connected to the first gripping apparatus; a second control module connected to the second gripping apparatus; and an actuator module connected to the actuator drive. The first control module can control a phase of the first phase change material, the first phase change material being either in a solid phase state in which the first phase change material grips the stick or a liquid phase state in which the first phase change material loosens its grip on the stick such that the stick is capable of moving through the first phase change material along the axial direction. The second control module can control a phase of the second phase change material, wherein the second phase change material is either in a solid phase state in which the second phase change material grips the stick or a liquid phase state in which the second phase change material loosens its grip on the stick such that the stick is capable of moving through the second phase change material along the axial direction. The actuator module can control the relative position between a first end of the actuator drive and a second end of the actuator drive along the axial direction.

The actuator module can provide a temporally-varying signal to the actuator drive; and a position of the stick along the axial direction can be adjusted by adjusting the one or more signals provided to the first gripping apparatus and to the second gripping apparatus. The position of the stick along the axial direction can be adjusted without adjusting a signal provided to the actuator drive.

The controller can further include a master control module connected to the first control module, the second control module, and the actuator module. The master control module can control the signals provided to each of the first control module, the second control module, and the actuator module.

The second gripping apparatus can be thermally independent of the first gripping apparatus.

In other general aspects, a positioning apparatus includes: a single actuator drive movable along an axial direction; a plurality of axial holders, each axial holder configured to receive a stick and each axial holder being fixed to the single actuator drive; and a controller in communication with the single actuator drive and with the plurality of axial holders. The controller is configured to: provide an actuation signal to the single actuator drive; and provide at least one independent signal to each of the axial holders. The position of each stick is independently adjustable along the axial direction by the adjustment of the provided at least one independent signal to each of the axial holders without adjusting the provided actuation signal to the single actuator drive.

Implementations can include one or more of the following features. The single actuator drive can include a first end and a second end; and the first and second ends can be movable relative to each other along the axial direction. Each axial holder can include a first gripping apparatus fixed to the first end of the single actuator drive and a second gripping apparatus fixed to the second end of the single actuator drive. The second gripping apparatus can be aligned along an axial direction with the first gripping apparatus. For each axial holder: the first gripping apparatus can be configured to receive a first region of the stick that is received in that axial holder and the second gripping apparatus can be configured to receive a second region of the stick that is received in that axial holder. For each axial holder: the first gripping apparatus can include a phase change material that is configured to receive the first region of the stick that is received in that axial holder; and the second gripping apparatus can include a phase change material that is configured to receive the second region of the stick that is received in that axial holder.

The actuation signal can be provided to the single actuator drive by providing a temporally-varying signal to the single actuator drive, the temporally-varying signal controlling an axial position associated with the single actuator drive.

Each axial holder can be configured to interact with at least two interaction regions of its associated stick. At each interaction region, the stick can be received in a gripping apparatus. At least one independent signal can be provided to each of the axial holders by providing an independent signal to each gripping apparatus in each axial holder. Each gripping apparatus can include a temperature adjusting device; and a phase change material thermally coupled with the temperature adjusting device such that a temperature change in the temperature adjusting device causes a temperature change in the phase change material. The independent signal can be provided to a gripping apparatus by providing an independent signal to the temperature adjusting device, and the state of the phase change material can be selected by adjustment of the provided independent signal to the temperature adjusting device thermally coupled with the phase change material.

In other general aspects, a method includes: providing a single actuation signal to a single actuator drive, wherein the single actuation signal controls a movement of the single actuator drive along an axial direction; providing an independent signal to each axial holder of a plurality of axial holders, wherein each axial holder receives a stick and each axial holder is fixed to the single actuator drive; and independently adjusting a position of a stick along the axial direction by adjusting the provided independent signal to the axial holder that receives that stick and without adjusting the provided actuation signal to the single actuator drive.

Implementations can include one or more of the following features. For example, the single actuation signal can be provided to the single actuator drive by controlling a relative movement between a first end of the single actuator drive and a second end of the single actuator drive along the axial direction. The single actuation signal can be provided to the single actuator drive by providing a temporally-varying signal to the single actuator drive, the temporally-varying signal controlling an axial position associated with the single actuator drive.

An independent signal can be provided to an axial holder by providing an independent signal to a gripping apparatus in that axial holder. The independent signal can be provided to a gripping apparatus by providing an independent signal to a temperature adjusting device of the gripping apparatus. The method can further include selecting a state of a phase change material thermally coupled to the temperature adjusting device by adjusting the provided independent signal to the temperature adjusting device thermally coupled with that phase change material.

In some general aspects, a method includes providing a single actuation signal to a single actuator drive, wherein the single actuation signal controls a movement of the single actuator drive along an axial direction; providing an independent signal to each axial holder of a plurality of axial holders, wherein each axial holder receives a stick and each axial holder is fixed to the single actuator drive; and independently adjusting a position of a stick along the axial direction by adjusting the provided independent signal to the axial holder that receives that stick and without adjusting the provided actuation signal to the single actuator drive.

The single actuation signal can be provided to the single actuator drive by controlling a relative movement between a first end of the single actuator drive and a second end of the single actuator drive along the axial direction. The single actuation signal can be provided to the single actuator drive by providing a temporally-varying signal to the single actuator drive, the temporally-varying signal controlling an axial position associated with the single actuator drive.

An independent signal can be provided to an axial holder by providing an independent signal to a gripping apparatus of that axial holder. The independent signal can be provided to a gripping apparatus by providing an independent signal to a temperature adjusting device of the gripping apparatus. Moreover, the method can include selecting a state of a phase change material thermally coupled to the temperature adjusting device by adjusting the provided independent signal to the temperature adjusting device thermally coupled with that phase change material.

DESCRIPTION OF DRAWINGS

FIG. 2A is a side cross-sectional view of an implementation of the gripping apparatus of FIG. 1, in which the stick is gripped;

FIG. 2B is a top cross-sectional view of the implementation of the gripping apparatus of FIG. 1, in which the stick is gripped;

FIG. 3A is a side cross-sectional view of an implementation of the gripping apparatus of FIG. 1, in which the stick is released;

FIG. 3B is a top cross-sectional view of the implementation of the gripping apparatus of FIG. 1, in which the stick is released;

FIG. 4A is a side cross-sectional view and FIG. 4B is a top cross-sectional view of an implementation of a temperature adjusting device of a gripping apparatus;

FIG. 5A is a side cross-sectional view and FIG. 5B is a top cross-sectional view of an implementation of a temperature adjusting device of a gripping apparatus;

FIGS. 7A-7E show side cross-sectional view of an implementation of steps of a procedure for manufacturing a gripping apparatus such as the gripping apparatus of FIG. 1;

FIG. 9 is a block diagram of an implementation of a controller of the positioning apparatus of FIG. 8;

FIG. 10A shows side cross-sectional views of the positioning apparatus of FIG. 8 at distinct times in an exemplary signal cycle during which aspects of the positioning apparatus are adjusted to thereby affect a movement of a stick along a −z direction of a z axis;

FIG. 10B shows a timing diagram of three signal amplitudes versus time that correlates with each of the times depicted in FIG. 10A;

FIG. 11A shows side cross-sectional views of the positioning apparatus of FIG. 8 at distinct times in an exemplary signal cycle during which aspects of the positioning apparatus are adjusted to thereby affect a movement of a stick along a +z direction of a z axis;

FIG. 11B shows a timing diagram of three signal amplitudes versus time that correlates with each of the times depicted in FIG. 11A;

FIGS. 16A-16E a block diagrams, each showing an implementation of a configuration of sticks in the positioning apparatus of FIG. 13;

DETAILED DESCRIPTION

Figure 1:
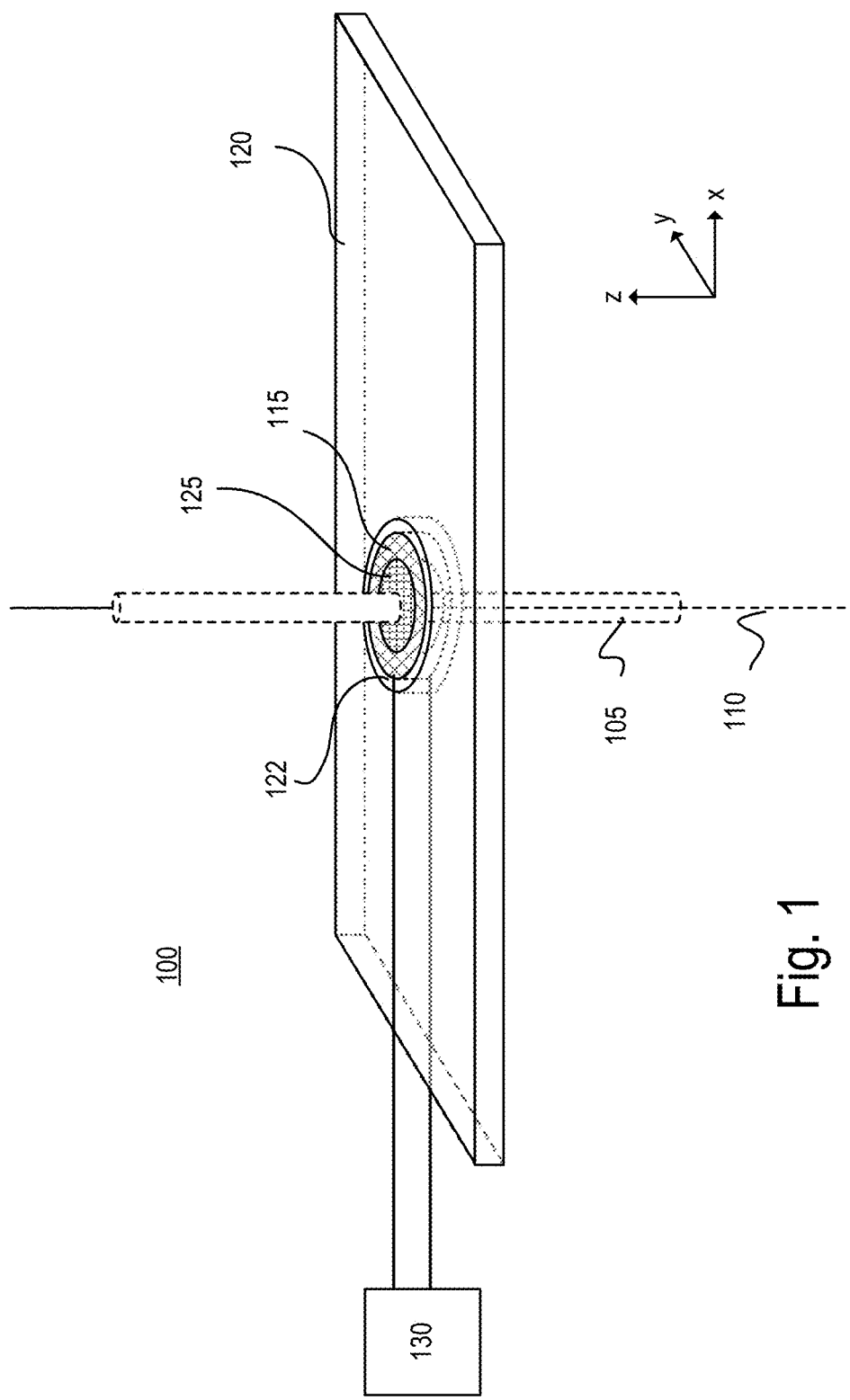
FIG. 1 is a schematic perspective view of a gripping apparatus configured to control a grip on and a motion of a stick.

Referring to FIG. 1, a gripping apparatus 100 is designed to control a grip on and also a motion of a stick 105. The sizes and geometry of features and elements in FIG. 1 are exaggerated to show details. The stick 105 can be any structure, device, or apparatus that generally extends along an axial direction 110. The stick 105 can be a solid structure or a hollow structure or a more complex structure made up of more than one material or region. In some implementations, the stick 105 can be used to measure one or more properties of some other element. In other implementations, the stick 105 can be used as an actuator to effect or modify one or more characteristics of another element. For example, the stick 105 can include an electrical conductor (such as a cable or wire); a measurement probe; a capillary tube; an optical waveguide; an optical fiber; a carbon fiber or filament; or a sonic waveguide. If the stick 105 is a measurement probe, then it could include an electrical testing probe, a silicon probe, an electrical recording probe, or an ultrasonic probe.

The stick 105 can be made of any material that is capable of withstanding motion without fracturing or bending or kinking. Thus, the stick 105 has a level of rigidity that enables it to be gripped as well as released and moved. A cross section of the stick 105 taken along a plane that is perpendicular to the axial direction 110 can have any geometric shape and it may or may not have symmetry. For example, the cross section can be a circular shape, a polygonal shape, an oval shape, or an irregular asymmetric shape.

The gripping apparatus 100 includes a temperature adjusting device 115 held or fixed in a substrate 120, and a phase change material 125. The substrate 120 defines an open region 122 that is large enough to accommodate the phase change material 125 as well as the stick 105 and any other components that may be used during assembly or manufacturing. The phase change material 125 is thermally coupled to the temperature adjusting device 115. This means that a temperature change in the temperature adjusting device 115 causes a temperature change in the phase change material 125. The stick 105 extends through the phase change material 125.

The gripping apparatus 100 also includes a controller 130. The controller 130 is connected to the temperature adjusting device 115 and is configured to send a signal to the temperature adjusting device 115 to change its temperature. The change in temperature affected at the temperature adjusting device 115 causes the temperature of the phase change material 125 that is thermally coupled with the temperature adjusting device 115 to change as well.

The phase change material 125 is a material that is able to transition between two distinct phases of matter as a result of a change in temperature. For example, the phase change material 125 can transition between a solid state and a liquid state. In some implementations, the phase change material 125 includes wax; paraffin wax; or alkane hydrocarbon. The alkane hydrocarbon can be any one or more of: n-octacosane, n-heptacosane, n-hexacosane, n-pentacosane, n-tetracosane, n-docosane, n-tricosane, n-heneicosane, n-eicosane, n-nonadecane, n-octadecane, n-heptadecane, n-hexadecane, n-pentadecane, n-tetradecane, and n-tridecane.

When in a liquid state, the phase change material 125 is held within the open region 122 by way of capillary action (and without the assistance of or in opposition to other external forces such as gravity). This happens because the adhesive forces, that is, the intermolecular attractive forces between the phase change material 125 and the solid surrounding surface of one or more of the temperature adjusting device 115 and the substrate 120, are stronger than the cohesive forces within the phase change material 125. If the size of the open region 122 (for example, a diameter taken in the plane perpendicular to the axial direction 110) is sufficiently small, then the combination of surface tension (which is caused by cohesion within the liquid) and adhesive forces act together to keep the phase change material 125 in the open region 122. In this way, the phase change material 125 remains within the open region 122 even if it is in the liquid state. The amount of phase change material 125 that is held within the open region 122 can be adjusted during assembly so that any expansion of the phase change material 125 during changes in phase is maintained within the open region 122. Thus, even if the phase change material 125 expands with a change in temperature, it can still remain contained in the open region 122. Additionally, in some implementations, the material of the phase change material 125 is not chemically reactive or attracted to the material of the stick 105.

The substrate 120 is generally defined in a plane that is perpendicular to the axial direction 110. For example, if the axial direction 110 is defined as the z axis, then the substrate 120 extends along the x-y plane. The substrate 120 also has a thickness along the z axis. In some implementations, the substrate 120 includes a printed circuit board. In such implementations, as discussed below, the communication channel (which can be an electrical connection) between the temperature adjusting device 115 and the controller 130 can be formed in the printed circuit board.

The controller 130 can include one or more of digital electronic circuitry, computer hardware, firmware, software, and a power supply. The controller 130 includes memory, which can be read-only memory and/or random-access memory. Storage devices suitable for tangibly embodying computer program instructions and data include all forms of non-volatile memory, including, by way of example, semiconductor memory devices, such as EPROM, EEPROM, and flash memory devices; magnetic disks such as internal hard disks and removable disks; magneto-optical disks; and CD-ROM disks. The controller 130 can also include one or more input devices (such as a keyboard, touch screen, microphone, mouse, hand-held input device, etc.) and one or more output devices (such as a speaker or a monitor).

The controller 130 includes one or more programmable processors, and one or more computer program products tangibly embodied in a machine-readable storage device for execution by a programmable processor. The one or more programmable processors can each execute a program of instructions to perform desired functions by operating on input data and generating appropriate output. Generally, the processor receives instructions and data from memory. Any of the foregoing may be supplemented by, or incorporated in, specially designed ASICs (application-specific integrated circuits). The controller 130 includes at least one module that includes a set of computer program products executed by one or more processors such as the processors. Moreover, the module can access data stored within the memory. The module can be in communication with a dedicated other component of the gripping apparatus 100 (for example, the temperature adjusting device 115).

Although the controller 130 is represented as a box (in which all of its components can be co-located), it is possible for the controller 130 to be made up of components that are physically remote from each other. In general, the controller 130 can perform functions not discussed herein.

The change of phase in the phase change material 125 is discussed with reference to FIGS. 2A-3B. In FIGS. 2A and 2B, the stick 105 is gripped, which means that it is fixed relative to the gripping apparatus 100 and is therefore prevented from moving relative to the gripping apparatus 100. By contrast, in FIGS. 3A and 3B, the stick 105 is released, which means that the stick 105 is capable of moving relative to the gripping apparatus 100. For example, the stick 105 is capable of moving along the axial direction 110.

When the phase change material 125 is at a temperature below a first transition temperature T1 (FIGS. 2A and 2B), the phase change material 125 is in a solid state. In this state, the phase change material 125 grips the stick 105 that is within the phase change material 125. The first transition temperature T1 is defined as that temperature at which the phase change material 125 is fully in the solid state after previously being in the liquid state.

When the phase change material 125 is at a temperature above a second transition temperature T2 (FIGS. 3A and 3B), the phase change material 125 is in a liquid state. In this state, the phase change material 125 loosens its grip on the stick 105 such that the stick 105 is capable of moving through the phase change material 125. The second transition temperature T2 is defined as that temperature at which the phase change material 125 is fully in the liquid state after previously being in the solid state.

Moreover, the transition between the solid state and the liquid state at the first transition temperature T1 or the second transition temperature T2 occurs at an operating temperature suitable for the gripping apparatus 100.

When the phase change material 125 is at a temperature above the second transition temperature T2, the stick 105 is capable of moving through the phase change material 125 along the z axis that is perpendicular to the x-y plane.

In some implementations, depending on the application of the stick 105, the first transition temperature T1 and the second transition temperature T2 can be at or near room temperature (for example, 20-25° C.). In other implementations, the first transition temperature T1 and the second transition temperature T2 can be at or near at a temperature of a living organism (for example, 36-43° C.). In other implementations, the first transition temperature T1 and the second transition temperature T2 can be below room temperature, or above room temperature.

The first transition temperature T1 can be equal to the second transition temperature T2. However, because of hysteresis, it is possible and likely that the transition temperatures T1 and T2 are not equal. The actual transition temperatures T1 and T2 depends on the previous state of the gripping apparatus 100. For example, the first transition temperature T1 is less than the second transition temperature T2. Additionally, as discussed above, the first transition temperature T1 is defined as that temperature at which the phase change material 125 is fully in the solid state after previously being in the liquid state. It is possible that the phase change material 125 remains in a fully solid state at a temperature above the first transition temperature T1 if the phase change material 125 is transitioning from a fully solid state to a liquid state. Similarly, it is possible that the phase change material 125 remains in a fully liquid state at a temperature below the second transition temperature T2 if the phase change material 125 is transitioning from a fully liquid state to a solid state.

Additionally, there may exist intermediate phases within the range of temperatures between the first transition temperature T1 and the second transition temperature T2 for some phase change materials 125.

The temperature adjusting device 115 is a device that is configured to change its temperature and enable heat transfer between the temperature adjusting device 115 and the phase change material 125. Moreover, the temperature adjusting device 115 is configured to be held in place in the substrate 120. In some implementations, the temperature of the temperature adjusting device 115 is modified or changed by a change in current that is applied to the temperature adjusting device 115. Thus, the temperature adjusting device 115 can include an element that is able to conduct current but has a high enough resistance to enable its temperature to change by a suitable amount with a change in current.

Referring to FIGS. 4A-6B, various implementations of the temperature adjusting device 115 are shown that are based on this resistive temperature control. The stick 105 is not shown in FIGS. 4A-6B but would be placed in and received in the open region 122.

In FIGS. 4A and 4B, the temperature adjusting device 115 is a resistive material 415 that is formed in or deposited in the open region 122. The resistive material 415 can be any metal that is conductive and has enough resistance to enable temperature adjustment. The resistive material 415 is formed so that it bonds to the interior surface of the substrate 120 that defines the open region 122. In some implementations, the resistive material 415 can be a carbon paste that coats the interior surface of the substrate 120 that defines the open region 122.

In FIGS. 5A and 5B, the temperature adjusting device 115 is a chip resistor 515 embedded within the open region 122 that receives the phase change material 125. In this way, the chip resistor 515 is in thermal communication with the phase change material 125.

Figure 6A:
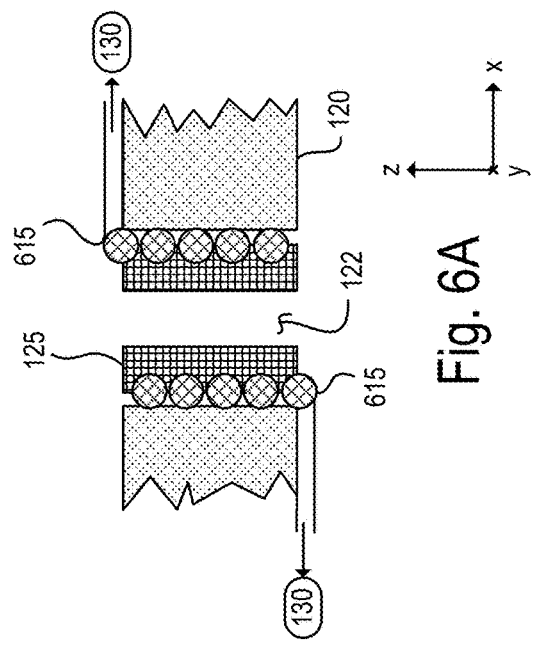
FIG. 6A is a side cross-sectional view and FIG. 6B is a top cross-sectional view of an implementation of a temperature adjusting device of a gripping apparatus.
Figure 6B:
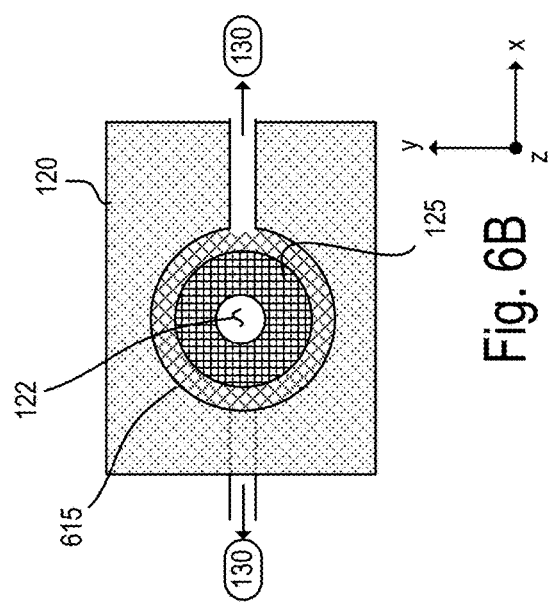

In FIGS. 6A and 6B, the temperature adjusting device 115 is a resistive conductive wire 615 that is wound into a spiral shape inside the open region 122 of the substrate 120. The wire 615 can be made of a metal alloy such as nichrome, which is an alloy of nickel and chrome.

In these implementations, the controller 130 includes a power source that supplies a current to the resistive element (such as the resistive material 415, the chip resistor 515, or the conductive wire 615) by way of electrically conductive elements 116, 117 (such as contacts or leads).

Referring to FIGS. 7A-7E, the gripping apparatus 100 is formed as follows. As shown in FIG. 7A, the substrate 120 is selected. As discussed above, the substrate 120 can be a blank region of a printed circuit board, and the printed circuit board can include other structures or regions not shown in FIGS. 7A-7E. Moreover, while not shown in FIGS. 7A-7E, it is possible for these other structures or regions of the printed circuit board to have different or specialized thermal properties. As shown in FIG. 7B, the open region 122 is formed in the substrate 120. The open region 122 can be formed by drilling a hole into the substrate 120 or using a milling machine or any suitable device for removing the material of the substrate 120. As shown in FIG. 7C, the temperature adjusting device 115 is formed so that it is held or fixed in the substrate 120. For example, the temperature adjusting device 115 can be held or fixed in the substrate 120 by gluing, epoxy, or embedding. The temperature adjusting device 115 can be formed in the open region 122 or adjacent to the open region 122, as long as it is located to be in thermal communication with the phase change material 125. If the temperature adjusting device 115 is the resistive conductive wire 615, then it can be wound inside the open region 122 touching the substrate 120. If the temperature adjusting device 115 is the resistive material 415 then it can be painted on, deposited on, plated on, or soldered into the open region 122, touching the substrate 120. If the temperature adjusting device 115 is the chip resistor 515, then it can be snapped or embedded into an opening such as the open region 122 and fixed into place by connection with the conductive elements 116, 117.

As shown in FIG. 7D, the phase change material 125 is deposited in the open region 122 so that it is in thermal communication with the temperature adjusting device 115. One way to deposit the phase change material 125 is to melt the phase change material 125 so that it is in a liquid state. The liquid form of the phase change material 125 can be drawn up or into the open region 122 using capillary forces or action in a wicking process. Once the phase change material 125 is fully deposited into the open region 122, as while the phase change material 125 is still in its liquid state, the stick 105 is inserted into the phase change material 125 and electrical connections are made between the temperature adjusting device 115 and the controller 130.

The gripping apparatus 100 can be formed in a manner that is different from that described with reference to FIGS. 7A-7E. For example, in other implementations, the phase change material 125 is added after the stick 105 is inserted into or through the open region 122.

Figure 8:
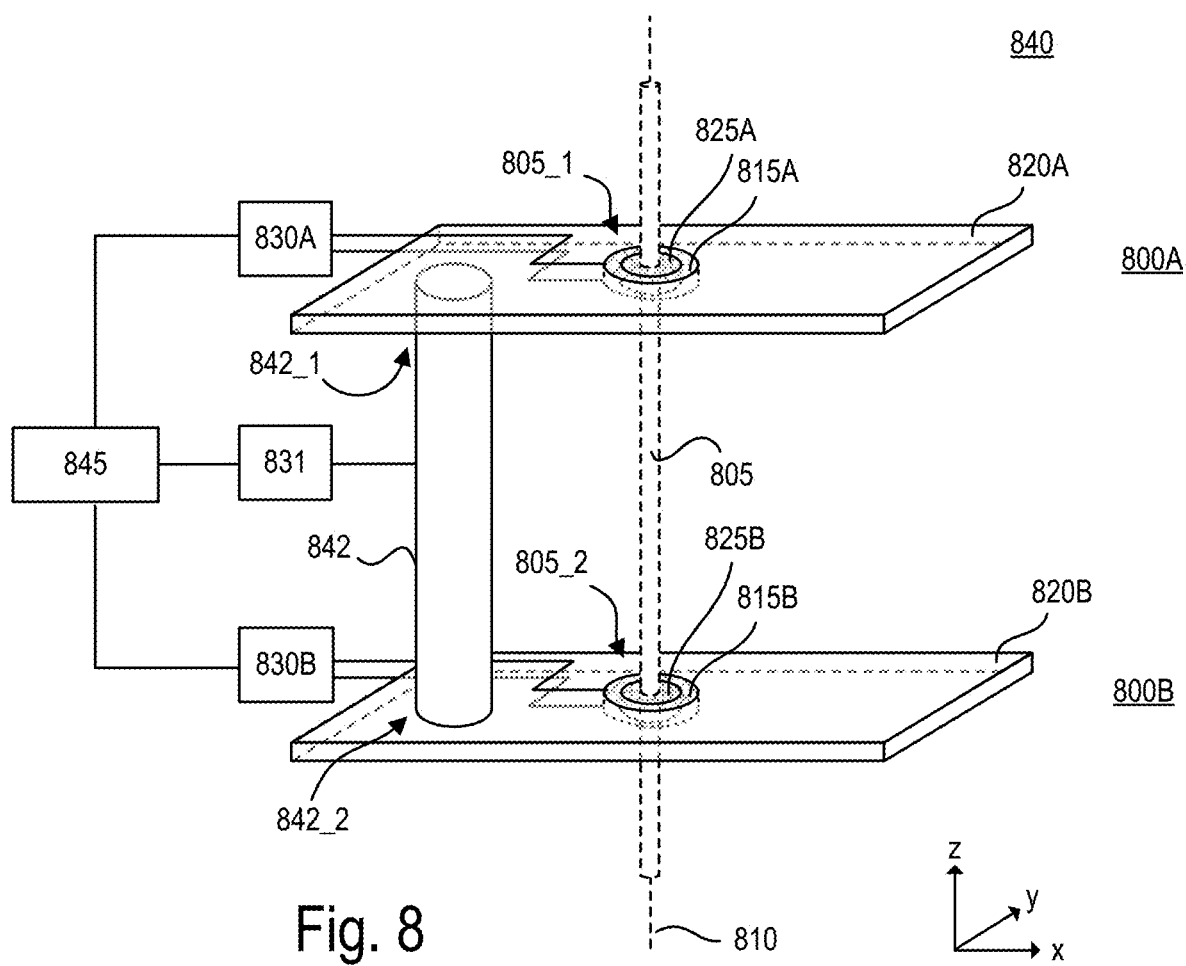
FIG. 8 is a schematic perspective view of a positioning apparatus including the gripping apparatus of FIG. 1 and configured to control a grip on and a motion of a stick.

Referring to FIG. 8, the gripping apparatus 100 can be used in a positioning apparatus 840 that is designed to move a stick 805 along an axial direction 810, which is parallel with the z axis. The stick 805 is shown for reference in FIG. 8 but is not necessarily a part of the positioning apparatus 840. The positioning apparatus 840 includes an actuator drive 842 movable along the axial direction 810. In some implementations, the actuator drive 842 can movable along only the axial direction 810.

The positioning apparatus 840 includes a first gripping apparatus 800A fixed to the actuator drive 842, a second gripping apparatus 800B fixed to the actuator drive 842, and a controller 845. The controller 845 is in communication with the first gripping apparatus 800A, the second gripping apparatus 800B, and the actuator drive 842 and thus the controller 845 controls the operation of each of the first gripping apparatus 800A, the second gripping apparatus 800B, and the actuator drive 842. Communication between the controller 845 and other elements of the positioning apparatus 840 can be wired or wireless.

The first and second gripping apparatuses 800A, 800B are designed like the gripping apparatus 100. Thus, the first gripping apparatus 800A includes a first phase change material 825A that is configured to receive a first region 805_1 of the stick 805. And, the second gripping apparatus 800B includes a second phase change material 825B that is aligned along the axial direction 810 with the first phase change material 825A and that is configured to receive a second region 805_2 of the stick 805.

The controller 845 is configured to provide one or more signals to the actuator drive 842, the first gripping apparatus 800A, and the second gripping apparatus 800B. In order to facilitate communications, the positioning apparatus 840 can include a sub-controller 830A in communication with the first gripping apparatus 800A, a sub-controller 830B in communication with the second gripping apparatus 800B, and a sub-controller 831 in communication with the actuator drive 842. Any communication between the controller 845 and the actuator drive 842 is conveyed by the sub-controller 831; any communication between the controller 845 and the first gripping apparatus 800A is conveyed by the sub-controller 830A; and any communication between the controller 845 and the second gripping apparatus 800B is conveyed by the sub-controller 830B.

The one or more signals provided to the first gripping apparatus 800A control a phase of the first phase change material 825A, and the one or more signals provided to the second gripping apparatus 800B control a phase of the second phase change material 825B. In this way, a position of the stick 805 along the axial direction 810 is adjusted or held constant depending on the one or more signals provided to the actuator drive 842, the first gripping apparatus 800A, and the second gripping apparatus 800B, as discussed in greater detail below. The controller 845 can be configured to adjust or control a timing and synchronization between the changes in the actuator drive 842 and the changes in the first and second phase change materials 825A, 825B.

The actuator drive 842 has a first end 842_1 and a second end 842_2. The first end 842_1 and the second end 842_2 are movable relative to each other. Thus, for example, the second end 842_2 can move while the first end 842_1 remains stationary in the x, y, z coordinate system, the first end 842_1 can move while the second end 842_2 remains stationary in the x, y, z coordinate system, or both the first end 842_1 and the second end 842_2 can move in the x, y, z coordinate system. If the first gripping apparatus 800A is fixed to the first end 842_1 of the actuator drive 842 and the second gripping apparatus 800B is fixed to the second end 842_2 of the actuator drive 842, then the relative movement between the first and second gripping apparatuses 800A, 800B can be controlled.

The actuator drive 842 can be any suitable drive that permits a relative motion between the first end 842_1 and the second end 842_2. Thus, the actuator drive 842 can be configured to perform one or more of the following controls: moving both the first end 842_1 and the second end 842_2 relative to each other; moving the first end 842_1 and maintaining the second end 842_2 stationary; and maintaining the first end 842_1 stationary and moving the second end 842_2.

In some implementations, the actuator drive 842 is a turnable screw configured to turn about the axial direction 810 to thereby translate the second end 842_2 relative to the first end 842_1 along the axial direction 810. In other implementations, the actuator drive 842 is a stepper motor configured to move the second end 842_2 relative to the first end 842_1 along the axial direction 810.

In other implementations, the actuator drive 842 is a piezoelectric actuator configured to move the second end 842_2 relative to the first end 842_1 along the axial direction 810. The voltage level applied to the piezoelectric material in the actuator is adjusted to thereby adjust a relative displacement between the first end 842_1 and the second end 842_2.

In still other implementations, the actuator drive 842 includes a shape memory alloy that is configured to expand when heated, which causes the second end 842_2 and the first end 842_1 to move farther apart, and to contract when cooled, which causes the second end 842_2 and the first end 842_1 to move closer together. An example of a shape memory alloy is nitinol, which is an alloy of nickel and titanium.

As mentioned, the first gripping apparatus 800A and the second gripping apparatus 800B can be designed like the gripping apparatus 100. Thus, the first gripping apparatus 800A includes a first temperature adjusting device 815A held in a first rigid substrate 820A. The first rigid substrate 820A defining a first open region that receives the first temperature adjusting device 815A. The first rigid substrate 820A is fixed to the actuator drive 842 to thereby fix the first gripping apparatus 800A to the actuator drive 842. The first phase change material 825A is held within the first open region and is thermally coupled with the first temperature adjusting device 815A such that a temperature change in the first temperature adjusting device 815A (which is affected under control of the controller 845) causes a temperature change in the first phase change material 825A. The controller 845 is in communication with the first temperature adjusting device 815A of the first gripping apparatus 800A such that the provision of the signal to the first gripping apparatus 800A from the sub-controller 830A controls the temperature of the first temperature adjusting device 815A to thereby control a temperature of the first phase change material 825A.

The second gripping apparatus 800B further includes a second temperature adjusting device 815B held in a second rigid substrate 820B, the second rigid substrate defining a second open region and being fixed to the actuator drive 842 to thereby fix the second gripping apparatus 800B to the actuator drive 842. The second phase change material 825B is held within the second open region and is thermally coupled with the second temperature adjusting device 815B such that a temperature change in the second temperature adjusting device 815B causes a temperature change in the second phase change material 825B. The controller 845 is in communication with the second temperature adjusting device 815B of the second gripping apparatus 800B such that the provision of the signal to the second gripping apparatus 800B from the sub-controller 830B controls the temperature of the second temperature adjusting device 815B to thereby control a temperature of the second phase change material 825B.

Referring also to FIG. 9, in some implementations, the controller 845 includes a first control module 946 in communication with the first gripping apparatus 800A by way of the sub-controller 830A, a second control module 947 in communication with the second gripping apparatus 800B by way of the sub-controller 830B, and an actuator module 948 in communication with the actuator drive 842 by way of the sub-controller 831. The controller 845 can also include a master module 949 that is in communication with one or more of the first control module 946, the second control module 947, and the actuator module 948.

In general, the controller 845 includes one or more of digital electronic circuitry, computer hardware, firmware, and software. The controller 845 includes memory 950, which can be read-only memory and/or random-access memory. Storage devices suitable for tangibly embodying computer program instructions and data include all forms of non-volatile memory, including, by way of example, semiconductor memory devices, such as EPROM, EEPROM, and flash memory devices; magnetic disks such as internal hard disks and removable disks; magneto-optical disks; and CD-ROM disks. The controller 845 can also include one or more input devices (such as a keyboard, touch screen, microphone, mouse, hand-held input device, etc.) and one or more output devices (such as a speaker or a monitor) 951.

The controller 845 includes one or more programmable processors 952, and one or more computer program products tangibly embodied in a machine-readable storage device for execution by a programmable processor. The one or more programmable processors can each execute a program of instructions to perform desired functions by operating on input data and generating appropriate output. Generally, the processor receives instructions and data from memory. Any of the foregoing may be supplemented by, or incorporated in, specially designed ASICs (application-specific integrated circuits).

Each module 946, 947, 948, 949 includes a set of computer program products executed by one or more processors such as the processors 952. Moreover, any of the modules 946, 947, 948, 949 can access data stored within the memory 950. Each module 946, 947, 948, 949 can be in communication with one or more other modules 946, 947, 948, 949.

Although the controller 845 is represented as a box (in which all of its components can be co-located), it is possible for the controller 845 to be made up of components that are physically remote from each other. For example, the first control module 946 can be physically co-located with the first gripping apparatus 800A or the sub-controller 830A.

The first control module 946 controls a phase of the first phase change material 825A. In particular, the first phase change material 825A is either in a solid phase state in which the first phase change material 825A grips the stick 805 or a liquid phase state in which the first phase change material 825A loosens its grip on the stick 805 such that the stick is capable of moving through the first phase change material 825A along the axial direction 810. Additionally, the second control module 947 controls a phase of the second phase change material 825B. The second phase change material 825B is either in a solid phase state in which the second phase change material 825B grips the stick 805 or a liquid phase state in which the second phase change material 825B loosens its grip on the stick 805 such that the stick 805 is capable of moving through the second phase change material 825B along the axial direction 810. The actuator module 948 controls the relative position between the first end 842_1 of the actuator drive 842 and a second end 842_2 of the actuator drive 842 along the axial direction 810.

The controller 845 can provide a temporally-varying signal to the actuator drive 842. For example, the actuator module 948, by way of the sub-controller 831, can provide the temporally-varying signal to the actuator drive 842. The temporally-varying signal can be a repeatable or somewhat repeatable signal, such as a periodic or pseudo-periodic signal or it can be an irregularly-shaped, yet changing signal that goes through steps to effect changes to the first and second gripping apparatuses 800A, 800B. It is not necessary for the periodic or pseudo-periodic signal to have a constant frequency. That is, the frequency with which certain aspects of the signal repeat can change or can include multiple frequencies. Moreover, it is possible for the signal to change its amplitude from each full cycle to the next full cycle.

A position of the stick 805 along the axial direction 810 is adjusted by adjusting the one or more signals provided from the first control module 946 to the first gripping apparatus 800A and from the second control module 947 to the second gripping apparatus 800B. Moreover, the position of the stick 805 along the axial direction 810 is adjusted without adjusting a signal provided from the actuator module 948 to the actuator drive 842.

The master control module 949 controls the signals provided to each of the first control module 946, the second control module 947, and the actuator module 948.

In other implementations, it is possible for the controller 845 to include fewer modules than what is described and shown in FIG. 9, or that one or more of the modules described and shown in FIG. 9 are combined into a single module or eliminated altogether.

Figure 12A:
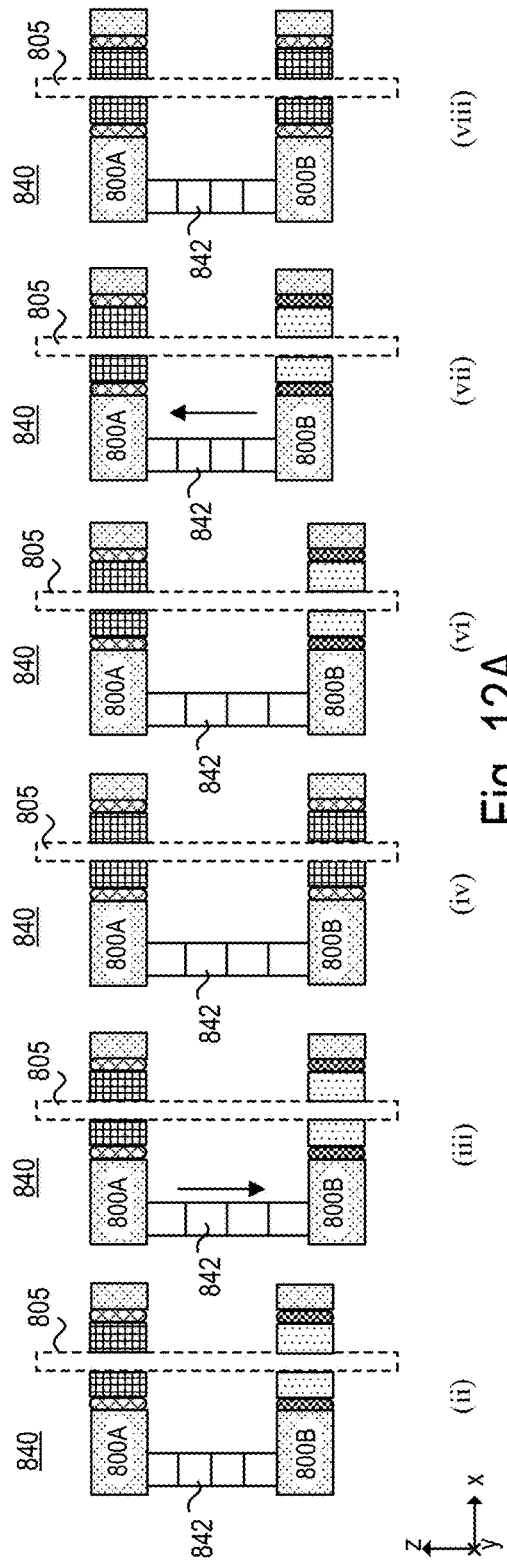
FIG. 12A shows side cross-sectional views of the positioning apparatus of FIG. 8 at distinct times in an exemplary signal cycle during which aspects of the positioning apparatus are adjusted but a stick remains stationary.
Figure 12B:
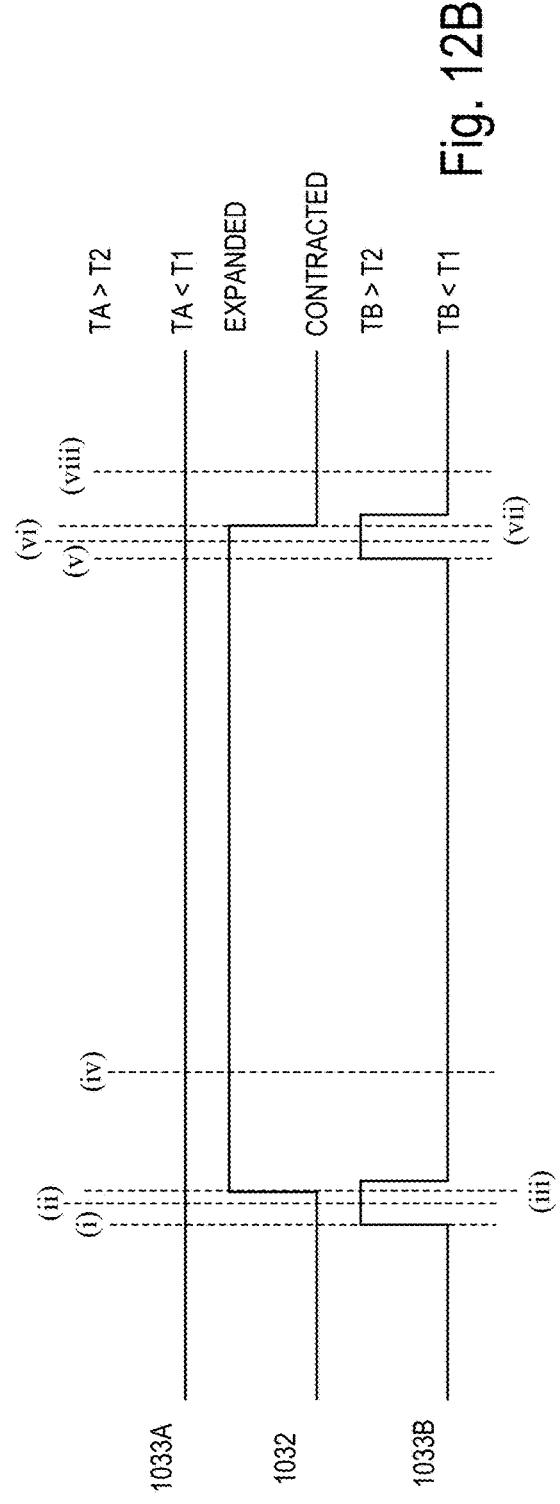
FIG. 12B shows a timing diagram of three signal amplitudes versus time that correlates with each of the times depicted in FIG. 12A.

The positioning apparatus 840 is configured to move the stick 805 along the axial direction 810. FIGS. 10A and 10B show an implementation of how the stick 805 is moved along the −z direction. FIGS. 11A and 11B show an implementation of how the stick 805 is moved along the +z direction. FIGS. 12A and 12B show an implementation of how the stick 805 remains stationary along the z axis even though the temporally-varying signal provided from the actuator module 948 to the actuator drive 842 is uninterrupted (and not halted). Each of these implementations are discussed next.

With reference to FIG. 10A, a side cross-sectional view of the positioning apparatus 840 is shown at eight distinct times [(i), (ii), (iii), (iv), (v), (vi), (vii), (viii)] in a signal cycle in order to affect the movement or translation of the stick 805 along the −z direction. FIG. 10B is a timing diagram showing the corresponding three signal amplitudes versus time (in arbitrary units). The top signal is a signal 1033A provided by the sub-controller 830A to the first temperature adjusting device 815A of the first gripping apparatus 800A. The signal 1033A provided to the first temperature adjusting device 815A controls a temperature of the first temperature adjusting device 815A, which therefore controls the temperature and a phase of the first phase change material 825A. The bottom signal is a signal 1033B provided by the sub-controller 830B to the second temperature adjusting device 815B of the second gripping apparatus 800B. The signal 1033B provided to the second temperature adjusting device 815B controls a temperature of the second temperature adjusting device 815B, which therefore controls the temperature and a phase of the second phase change material 825B. And, the middle signal is a signal provided by the sub-controller 831 to the actuator drive 842.

Initially, before time (i), the state of the positioning apparatus 840 is as follows. The signal 1033A is at an OFF amplitude or level, which means that the first temperature adjusting device 815A is below a first temperature and the first phase change material 825A is at a temperature TA that is below the first transition temperature T1. Thus, the first phase change material 825A of the first gripping apparatus 800A is in a solid state, and the first phase change material 825A grips the stick 805 at the first region 805_1. The signal 1033B is at an OFF amplitude or level, which means that the second temperature adjusting device 815B is below a first temperature and the second phase change material 825B is at a temperature TB that is below the first transition temperature T1. Thus, the second phase change material 825B of the second gripping apparatus 800B is in a solid state, and the second phase change material 825B grips the stick 805 at the second region 805_2. The stick 805 is fixed relative to the z axis. Additionally, the signal 1032 is at a LOW amplitude or level, and the voltage applied to the actuator drive 842 is at the LOW amplitude, which means that the actuator drive 842 is in a contracted state. An amplitude that is LOW can be a low non-zero value or can be zero or off.

At time (i) (FIG. 10B), the signal 1033A has been changed to an ON amplitude or level and the signal 1033B is at an OFF amplitude or level. Additionally, the signal 1032 is at a LOW amplitude or level, and the voltage applied to the actuator drive 842 is at the LOW amplitude, which means that the actuator drive 842 is in a contracted state.

After a period of time from time (i), at time (ii), the first temperature adjusting device 815A is above a second temperature and the first phase change material 825A reaches a temperature TA that is above the second transition temperature T2. Thus, the first phase change material 825A of the first gripping apparatus 800A is in a liquid state (depicted by the dotted fill in FIG. 10A(ii)), and the first phase change material 825A loosens its grip on the stick 805 at the first region 805_1. The signal 1033B remains at an OFF amplitude or level, which means that the temperature adjusting device 815B is below a first temperature and the second phase change material 825B is at a temperature TB that is below the first transition temperature T1. Thus, the second phase change material 825B of the second gripping apparatus 800B is in a solid state (depicted by a grid fill in FIG. 10A(ii)), and the second phase change material 825B grips the stick 805 at the second region 805_2. Additionally, the signal 1032 is still at a LOW amplitude or level, and the voltage applied to the actuator drive 842 is at the LOW amplitude, which means that the actuator drive 842 is in a contracted state. Because of this, even though the grip on the stick 805 is loosened at the first region 805_1, the stick 805 remains fixed relative to the z axis because the stick 805 is still gripped at the second region 805_2.

At time (iii), the signal 1033A remains at the ON amplitude, which means that the first phase change material 825A is at the temperature TA that is above the second transition temperature T2, and the first phase change material 825A of the first gripping apparatus 800A remains in the liquid state. Thus, the first phase change material 825A has a loosened grip on the first region 805_1 of the stick 805. The signal 1033B remains at an OFF amplitude, which means that the second phase change material 825B is at a temperature TB that is below the first transition temperature T1, and the second phase change material 825B of the second gripping apparatus 800B is in a solid state. Thus, the second phase change material 825B grips the second region 805_2 of the stick 805. Now, though, the signal 1032 transitions to a HIGH amplitude or level, and the voltage applied to the actuator drive 842 is at the HIGH amplitude, which means that the actuator drive 842 moves to an expanded state. In the expanded state, in this implementation, the second end 842_2 of the actuator drive 842 is moved along the −z direction relative to the first end 842_1 of the actuator drive 842. Because the second gripping apparatus 800B is fixed to the second end 842_2 of the actuator drive 842 at time (iii) and the grip on the stick 805 is loosened at the first region 805_1, the stick 805 is translated along the −z direction by an amount that corresponds to how much the second end 842_2 of the actuator drive 842 is moved.

At time (iv), the signal 1033A has been switched to an OFF amplitude for some time, and the first phase change material 825A reaches the temperature TA that is below the first transition temperature T1, and the first phase change material 825A of the first gripping apparatus 800A returns to the solid state, as depicted by the grid fill shown in FIG. 10A(iv). Thus, the first phase change material 825A grips the first region 805_1 of the stick 805. The signal 1033B remains at an OFF amplitude, which means that the second phase change material 825B is at a temperature TB that is below the first transition temperature T1, and the second phase change material 825B of the second gripping apparatus 800B is in a solid state. Thus, the second phase change material 825B maintains its grip on the second region 805_2 of the stick 805. The signal 1032 remains at a HIGH amplitude or level, and the voltage applied to the actuator drive 842 is at the HIGH amplitude, which means that the actuator drive 842 remains in the expanded state. Because the stick 805 is gripped at both the first and second regions 805_1, 805_2, the stick 805 remains stationary at this time relative to the z axis.

At time (v), the signal 1033A remains at the OFF amplitude, which means that the first phase change material 825A is at the temperature TA that is below the first transition temperature T1, and the first phase change material 825A of the first gripping apparatus 800A returns to the solid state. Thus, the first phase change material 825A grips the first region 805_1 of the stick 805. The signal 1033B is changed to an ON amplitude or level. And, the signal 1032 remains at a HIGH amplitude or level, and the voltage applied to the actuator drive 842 is at the HIGH amplitude, which means that the actuator drive 842 remains in the expanded state.

Eventually, after a period of time from time (v), such as at time (vi), the second phase change material 825B reaches a temperature TB that is above the second transition temperature T2, and the second phase change material 825B of the second gripping apparatus 800B is in a liquid state, as shown by the dotted fill in FIG. 10A(vi). Thus, the second phase change material 825B loosens its grip on the second region 805_2 of the stick 805. The signal 1032 remains at a HIGH amplitude or level, and the voltage applied to the actuator drive 842 is at the HIGH amplitude, which means that the actuator drive 842 remains in the expanded state. The stick 805 remains stationary at this time relative to the z axis even though the grip on the stick 805 is loosened at the second region 805_2 because the stick 805 is gripped at the first region 805_1.

At time (vii), the signal 1033A remains at the OFF amplitude, which means that the first phase change material 825A is at the temperature TA that is below the first transition temperature T1, and the first phase change material 825A of the first gripping apparatus 800A is in the solid state. Thus, the first phase change material 825A grips the first region 805_1 of the stick 805. The signal 1033B remains at the ON amplitude, which means that the second phase change material 825B is at a temperature TB that is above the second transition temperature T2, and the second phase change material 825B of the second gripping apparatus 800B is in a liquid state. Thus, the second phase change material 825B remains in a state in which its grip on the second region 805_2 of the stick 805 is loosened. The signal 1032 changes from the HIGH amplitude to the LOW amplitude, and the voltage applied to the actuator drive 842 switches to the LOW amplitude, which means that the actuator drive 842 changes to the contracted state. The stick 805 remains stationary at this time because the stick 805 is gripped at the first region 805_1, which is fixed to the first gripping apparatus 800A, which is not moving, and although the second gripping apparatus 800B is moving along the +z direction, the stick 805 does not move along because the second region 805_2 of the stick is not gripped by the second gripping apparatus 800B.

At time (viii), the signal 1033A remains at the OFF amplitude, which means that the first phase change material 825A is at the temperature TA that is below the first transition temperature T1, and the first phase change mate-rial 825A of the first gripping apparatus 800A is in the solid state. Thus, the first phase change material 825A grips the first region 805_1 of the stick 805. The signal 1033B was switched to the OFF amplitude after time (viii) and before time (viii), and eventually, at time (viii), the second phase change material 825B reaches a temperature TB that is below the first transition temperature T1, and the second phase change material 825B of the second gripping apparatus 800B is in the solid state, as depicted by the grid fill in FIG. 10A(viii). Thus, the second phase change material 825B has switched to the state in which it grips the second region 805_2 of the stick 805. The signal 1032 remains at the LOW amplitude, which means that the actuator drive 842 is in the contracted state. The stick 805 remains stationary at this time because the stick 805 is gripped at the first region 805_1 and at the second region 805_2.

The ON amplitude of the signal 1033A and 1033B as well as the time during which the signal 1033A, 1033B remains at the ON amplitude, and the ON voltage of the signal 1032 and the time during which the signal 1032 is at the ON voltage depend on factors such as the resistance, size, and materials of the phase change materials 825A, 825B and initial temperatures of various components of the first and second gripping apparatuses 800A, 800B.

In some implementations, the ON amplitude of the signal 1033A or 1033B can correspond to about tens or hundreds (for example, 10-200) milliamperes (mA) while the ON voltage of the signal 1032 supplied to the actuator drive 842 can be on the order of several tens or hundreds (for example, 10-200) volts (V). The time during which the signal 1033A or 1033B remains with an ON amplitude can be on the order of several, tens, or hundreds of (for example, 1-1000) milliseconds (ms) while the time during which the signal 1032 is at the ON voltage (and the actuator drive 842 is in the expanded state) can be on the order of a second or several seconds (for example, 0.1-10 s).

Moreover, it is possible that a temperature and an environment of the first gripping apparatus 800A is different from a temperature and an environment of the second gripping apparatus 800B during operation of the positioning apparatus 840, depending on the application and use of the positioning apparatus 840. For example, the second gripping apparatus 800B may be positioned closer to or in contact with a warm-bodied animal, which can raise the temperature of the second gripping apparatus 800B relative to the first gripping apparatus 800A (which would be farther from the warm-bodied animal).

It should also be noted that because of this, the first and second transition temperatures T1 and T2 of the first phase change material 825A may be distinct from the first and second transition temperatures T1 and T2 of the second phase change material 825B. For simplicity in description of FIGS. 10A, 10B, 11A, 11B, 12A, and 12B, it is assumed that when referencing the first and second transition temperatures T1 and T2, these are the values specific to the phase change material 825A or 825B being described.

With reference to FIG. 11A, a side cross-sectional view of the positioning apparatus 840 is shown at eight distinct times [(i), (ii), (iii), (iv), (v), (vi), (vii), (viii)] in a signal cycle in order to affect the movement or translation of the stick 805 along the +z direction. FIG. 11B is a timing diagram showing the corresponding three signal amplitudes (1033A, 1033B, and 1032) versus time (in arbitrary units).

Initially, before time (i), the state of the positioning apparatus 840 is as follows. The signal 1033A is at an OFF amplitude or level, and thus the first phase change material 825A of the first gripping apparatus 800A is in a solid state, and the first phase change material 825A grips the stick 805 at the first region 805_1. The signal 1033B is at an OFF amplitude or level, and thus the second phase change material 825B of the second gripping apparatus 800B is in a solid state, and the second phase change material 825B grips the stick 805 at the second region 805_2. The stick 805 is fixed relative to the z axis. Additionally, the signal 1032 is at a LOW amplitude or level, and the voltage applied to the actuator drive 842 is at the LOW amplitude, which means that the actuator drive 842 is in a contracted state.

At time (i), the signal 1033A remains at an OFF amplitude or level, which means that the first temperature adjusting device 815A is below a first temperature and the first phase change material 825A is at a temperature TB that is below the first transition temperature T1. Thus, the first phase change material 825A of the first gripping apparatus 800A is in a solid state, and the first phase change material 825A grips the stick 805 at the first region 805_1. The signal 1033B is changed to an ON amplitude or level. Additionally, the signal 1032 is at a LOW amplitude or level, and the voltage applied to the actuator drive 842 is at the LOW amplitude, which means that the actuator drive 842 is in a contracted state.

After a period of time beyond time (i), at time (ii), the second temperature adjusting device 815B reaches a second temperature and the second phase change material 825B is at a temperature TB that is above the second transition temperature T2. Thus, the second phase change material 825B of the second gripping apparatus 800B reaches a liquid state, as shown by the dotted fill in FIG. 11A(ii), and the second phase change material 825B loosens its grip on the stick 805 at the second region 805_2. At time (ii), the signal 1033A remains at an OFF amplitude or level, thus, the first temperature adjusting device 815A is below a first temperature and the first phase change material 825A is at a temperature TB that is below the first transition temperature T1. Thus, the first phase change material 825A of the first gripping apparatus 800A is in a solid state, as shown by the grid fill in FIG. 11A(ii), and the first phase change material 825A grips the stick 805 at the first region 805_1. Additionally, the signal 1032 is at a LOW amplitude or level, and the voltage applied to the actuator drive 842 is at the LOW amplitude, which means that the actuator drive 842 is in a contracted state. Even though the grip on the stick 805 is loosened at the second region 805_2, the stick 805 remains fixed relative to the z axis because the stick 805 is still gripped at the first region 805_1.

At time (iii), the signal 1033A remains at the OFF amplitude, which means that the first phase change material 825A is at a temperature TA that is below the first transition temperature T1, and the first phase change material 825A is in a solid state, as depicted by the grid fill in FIG. 11A(iii). Thus, the first phase change material 825A maintains its grip on the first region 805_1 of the stick 805. The signal 1033B remains at the ON amplitude, which means that the second phase change material 825B is at the temperature TB that is above the second transition temperature T2, and the second phase change material 825B of the second gripping apparatus 800B remains in the liquid state, as depicted by the dotted fill in FIG. 11A(iii). Thus, the second phase change material 825B maintains its loosened grip on the second region 805_2 of the stick 805. Now, though, the signal 1032 to the actuator drive 842 transitions to a HIGH amplitude or level, and the voltage applied to the actuator drive 842 is at the HIGH amplitude, which means that the actuator drive 842 moves to an expanded state. In the expanded state, in this implementation, the second end 842_2 of the actuator drive 842 is moved along the −z direction relative to the first end 842_1 of the actuator drive 842. Even though the second gripping apparatus 800B is fixed to the second end 842_2 of the actuator drive 842 at time (iii), because the grip on the stick 805 is loosened at the second region 805_2, the stick 805 does not translate along the −z direction with the second end 842_2 of the actuator drive 842.

At time (iv), the signal 1033A remains at an OFF amplitude, which means that the first phase change material 825A is at a temperature TA that is below the first transition temperature T1, and the first phase change material 825A is in a solid state, as depicted by the grid fill in FIG. 11A(iv). Thus, the first phase change material 825A maintains its grip on the first region 805_1 of the stick 805. The signal 1033B was switched to an OFF amplitude before time (iv), and by the time (iv), the second phase change material 825B reaches the temperature TB that is below the first transition temperature T1, and the second phase change material 825B of the second gripping apparatus 800B returns to the solid state, as depicted by the grid fill in FIG. 11A(iv). Thus, the second phase change material 825B grips the second region 805_2 of the stick 805. The signal 1032 remains at a HIGH amplitude or level, and the voltage applied to the actuator drive 842 is at the HIGH amplitude, which means that the actuator drive 842 remains in the expanded state. Because the stick 805 is gripped at both the first and second regions 805_1, 805_2, the stick 805 remains stationary at this time relative to the z axis.

At time (v), the signal 1033A has been changed to an ON amplitude or level, and the signal 1033B remains at the OFF amplitude, which means that the second phase change material 825B is at the temperature TB that is below the first transition temperature T1, and the second phase change material 825B of the second gripping apparatus 800B remains in the solid state and grips the second region 805_2 of the stick 805. Moreover, the signal 1032 remains at a HIGH amplitude or level, and the voltage applied to the actuator drive 842 is at the HIGH amplitude, which means that the actuator drive 842 remains in the expanded state.

After a period of time form time (v), at time (vi), the first phase change material 825A reaches a temperature TA that is above the second transition temperature T2, and the first phase change material 825A is in a liquid state, as depicted by the dotted fill in FIG. 11A(vi). Thus, the first phase change material 825A loosens its grip on the first region 805_1 of the stick 805. The signal 1033B remains at the OFF amplitude, which means that the second phase change material 825B is maintained at the temperature TB that is below the first transition temperature T1, and the second phase change material 825B of the second gripping apparatus 800B is in the solid state, as depicted by the grid fill in FIG. 11A(vi). Thus, the second phase change material 825B grips the second region 805_2 of the stick 805. The signal 1032 remains at a HIGH amplitude or level, and the voltage applied to the actuator drive 842 is at the HIGH amplitude, which means that the actuator drive 842 remains in the expanded state. The stick 805 remains stationary at this time relative to the z axis even though the grip on the stick 805 is loosened at the first region 805_1 because the stick 805 is gripped at the second region 805_2 and the actuator drive 842 is stationary.

At time (vii), the signal 1033A remains at the ON amplitude, which means that the first phase change material 825A is at a temperature TA that is above the second transition temperature T2, and the first phase change material 825A is in a liquid state, as depicted by a dotted fill in FIG. 11A(vii). Thus, the first phase change material 825A remains in a state in which its grip on the first region 805_1 of the stick 805 is loosened. The signal 1033B remains at the OFF amplitude, which means that the second phase change material 825B is maintained at the temperature TB that is below the first transition temperature T1, and the second phase change material 825B is in the solid state, as depicted by a grid fill in FIG. 11A(vii). Thus, the second phase change material 825B grips the second region 805_2 of the stick 805. The signal 1032 changes from the HIGH amplitude to the LOW amplitude, and the voltage applied to the actuator drive 842 switches to the LOW amplitude, which means that the actuator drive 842 changes to the contracted state. The stick 805 moves or translates along the +z direction as the second end 842_2 of the actuator drive 842 is moved along the +z direction relative to the first end 842_1 of the actuator drive 842 because the second gripping apparatus 800B is fixed to the second end 842_2 of the actuator drive 842.

At time (viii), the signal 1033A has been switched to the OFF amplitude, and enough time has passed so that the first phase change material 825A has reached a temperature TA that is below the first transition temperature T1, and the first phase change material 825A is now in the solid state, as depicted by the grid fill in FIG. 11A(viii). Thus, the first phase change material 825A has switched to the state in which it grips the first region 805_1 of the stick 805. The signal 1033B remains at the OFF amplitude, which means that the second phase change material 825B is at the temperature TB that is below the first transition temperature T1, and the second phase change material 825B is in the solid state. Thus, the second phase change material 825B grips the second region 805_2 of the stick 805. The signal 1032 remains at the LOW amplitude, which means that the actuator drive 842 is maintained in the contracted state. The stick 805 remains stationary at this time because the stick 805 is gripped at the first region 805_1 and at the second region 805_2.

With reference to FIG. 12A, a side cross-sectional view of the positioning apparatus 840 is shown at eight distinct times [(i), (ii), (iii), (iv), (v), (vi), (vii), (viii)] in a signal cycle in which the stick 805 remains stationary relative to the z axis even though the actuator drive 842 is operating to expand and contract. FIG. 12B is a timing diagram showing the corresponding three signal amplitudes (1033A, 1033B, and 1032) versus time (in arbitrary units).

In general, the stick 805 remains stationary at all times in this signal cycle because the signal 1033A provided to the first temperature adjusting device 815A remains at an OFF amplitude and thus the first phase change material 825A remains in a solid phase state, which means that it is always gripping the first end 842_1 of the actuator drive 842. This is depicted in FIG. 12A by the grid fill in the first phase change material 825A. The first gripping apparatus 800A is therefore fixed to the first end 842_1 of the actuator drive 842 at all times, and because the first end 842_1 remains stationary, the first region 805_1 of the stick 805 remains stationary.

Moreover, in order to prevent breakage because of the motion of the second end 842_2 of the actuator drive 842, the signal 1033B is adjusted in coordination with the signal 1032, as follows. The signal 1033B is switched an ON amplitude at time (i) and enough time is allowed to pass so that at time (ii), the second phase change material 825B of the second gripping apparatus 800B reaches a temperature TB that is above the second transition temperature T2 and is in the liquid state. This is done in advance of the translation of the second end 842_2 along the −z direction of the actuator drive 842 at time (iii). In this way, the second end 842_2 of the actuator drive 842 can move at time (iii) without applying a force to the stick 805 in the −z direction. Then, the signal 1033B is switched to an OFF amplitude, and after a period of time from this, at time (iv), the second phase change material 825B has managed to cool down enough and drops below the first transition temperature T1 so that the second phase change material 825B is now in a solid state, as depicted by the grid fill in FIG. 12A(iv).

At time (v), the signal 1033B is adjusted to an ON amplitude and after enough time has elapsed, at time (vi), the second phase change material 825B of the second gripping apparatus 800B reaches a temperature TB that is above the second transition temperature T2 and is in the liquid state, as depicted by the dotted fill in FIG. 12A(vi). This is done in advance of switching the signal 1032 to a LOW amplitude or level at time (vii), which causes the translation of the second end 842_2 along the +z direction of the actuator drive 842 at time (vii) to enable the second end 842_2 of the actuator drive 842 to move at time (vii) without applying a force to the stick 805 in the +z direction. The signal 1033B is again switched to an OFF amplitude, and after a period of time from this, at time (viii), the second phase change material 825B has managed to cool down enough and drops below the first transition temperature T1 so that the second phase change material 825B is now in a solid state, as depicted by the grid fill in FIG. 12A(viii).

In general, if top (the first) temperature adjusting device 815A remains at an OFF amplitude and the bottom (the second) temperature adjusting device 815B is at an ON amplitude, then the stick 805 is fixed in the axial direction. In general, if top (the first) temperature adjusting device 815A is at an ON amplitude and the bottom (the second) temperature adjusting device 815B is at an OFF amplitude, then the stick 805 is movable in the axial direction. In these implementations, the first temperature adjusting device 815A and the second temperature adjusting device 815B are never at the ON amplitude or the OFF amplitude at the same time during motion of the stick 805.

Figure 13:
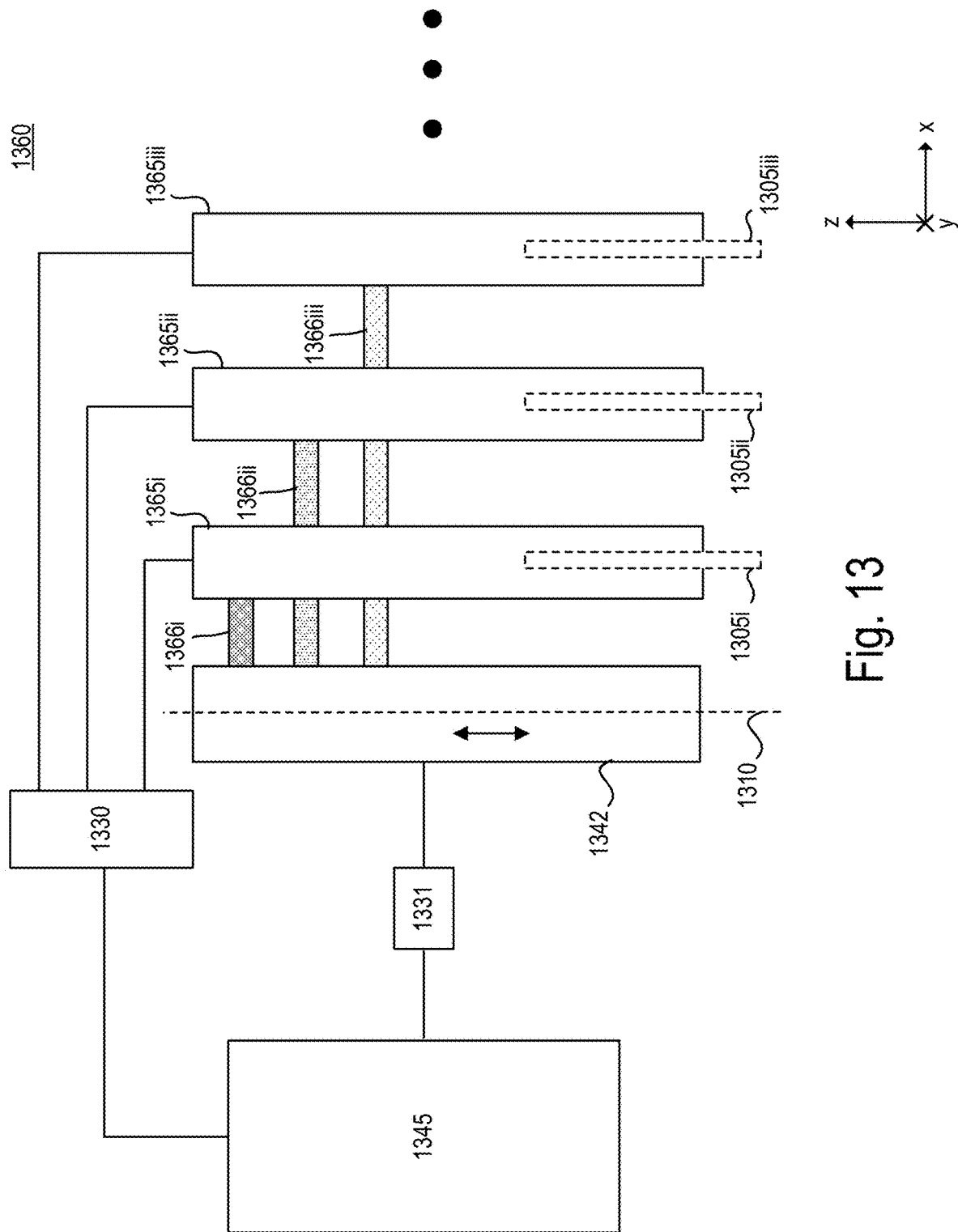
FIG. 13 is a block diagram of an implementation of a positioning apparatus designed to independently translate each of a plurality of sticks along an axial direction of that stick using an actuator drive.

Referring also to FIG. 13, a positioning apparatus 1360 is designed to independently translate each stick of a plurality of sticks 1305*i*, 1305*ii*, 1305*iii*, etc. along an axial direction of that stick using a single actuator drive 1342 movable along its own axial direction 1310, which is parallel with the z axis. The sticks 1305*i*, 1305*ii*, 1305*iii* are shown for reference in FIG. 13 but are not necessarily a part of the positioning apparatus 1360. Moreover, while three sticks 1305*i*, 1305*ii*, 1305*iii* are shown, fewer or greater than three sticks can be controlled by the positioning apparatus 1360.

The positioning apparatus 1360 includes a plurality of axial holders 1365*i*, 1365*ii*, 1365*iii*, etc. Each axial holder 1365*i*, 1365*ii*, 1365*iii* is configured to receive a respective stick 1305*i*, 1305*ii*, 1305*iii*. Additionally, each axial holder 1365*i*, 1365*ii*, 1365*iii* is fixed to the actuator drive 1342 at respective fixing mechanisms 1366*i*, 1366*ii*, 1366*iii*.

The positioning apparatus 1360 includes a controller 1345 in communication with the single actuator drive 1342 (for example, via the sub-controller 1331), and with the plurality of axial holders 1365*i*, 1365*ii*, 1365*iii* (for example, via a sub-controller 1330). The controller 1345 is configured to provide an actuation signal to the single actuator drive 1342 (by way of the sub-controller 1331). The controller 1345 is also configured to provide at least one independent signal to each of the axial holders 1365*i*, 1365*ii*, 1365*iii* by way of the sub-controller 1330). The position of each stick 1305*i*, 1305*ii*, 1305*iii* can be independently adjustable along its respective axial direction (which is parallel with the z axis and the axial direction 1310) by the adjustment of the provided at least one independent signal to each of the axial holders 1365*i*, 1365*ii*, 1365*iii* without adjusting the provided actuation signal to the single actuator drive 1342, as long as each axial holder 1365*i*, 1365*ii*, 1365*iii* is thermally independent of the other axial holders 1365*i*, 1365*ii*, 1365*iii*.

In particular, the actuation signal to the actuator drive 1342 can be a temporally-varying signal that toggles between a low amplitude (in which the voltage applied to the actuator drive 1342 is relatively low) and a high amplitude (in which the voltage applied to the actuator drive 13423 is relatively high).

Figure 14:
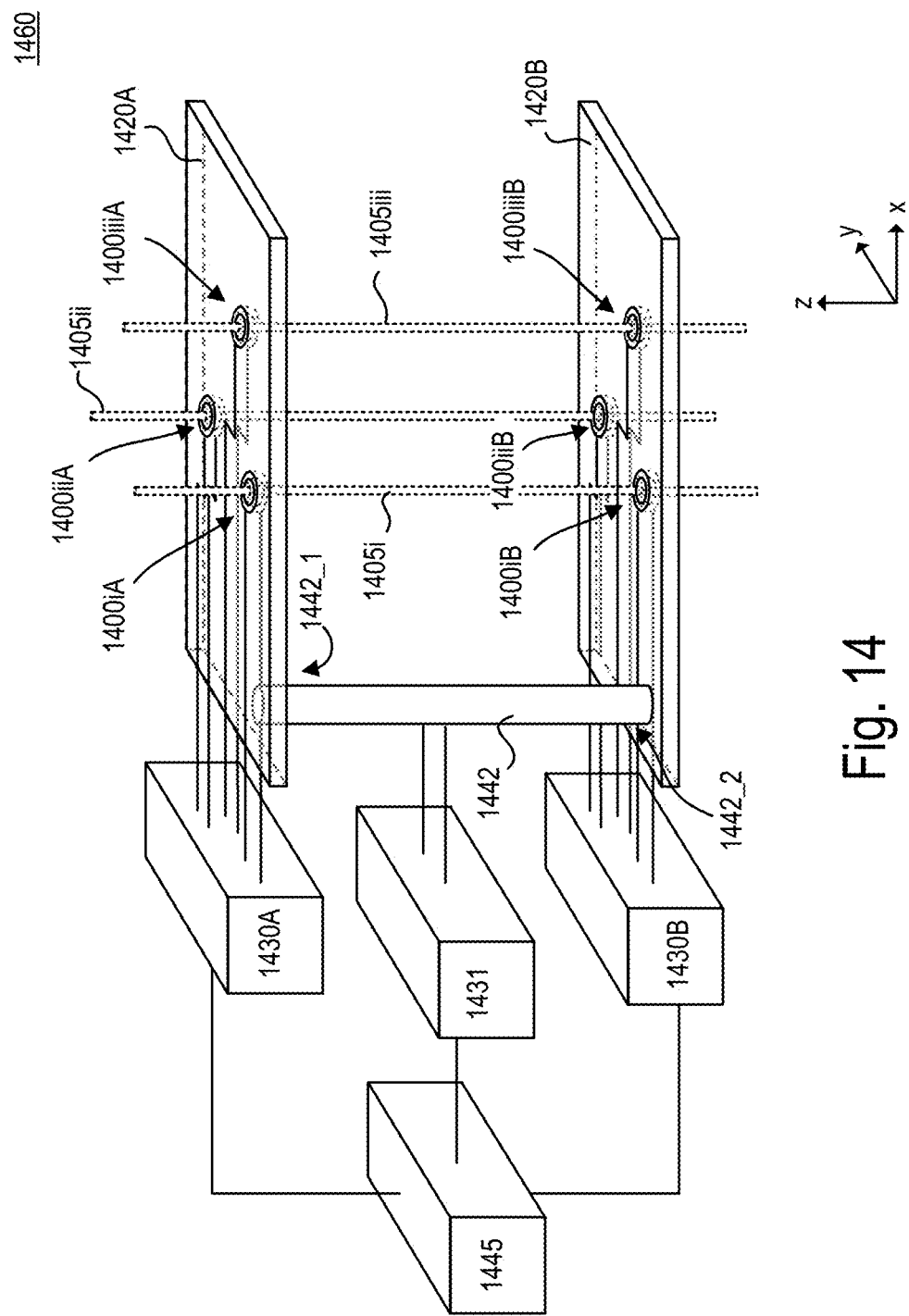
FIG. 14 is a perspective view of an implementation of the positioning apparatus of FIG. 13.
Figure 15:
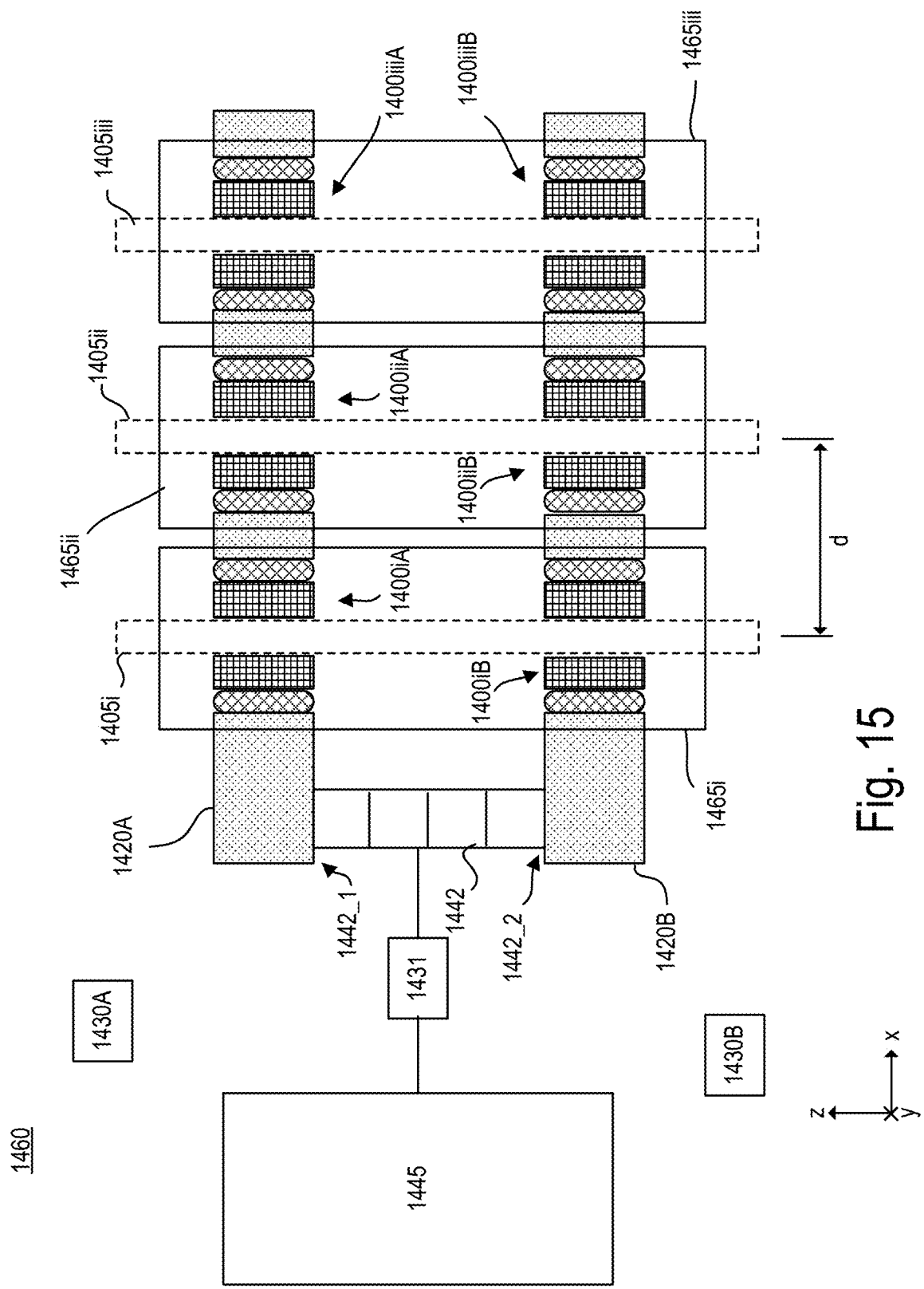
FIG. 15 is a partial side cross-sectional view of the implementation of the positioning apparatus of FIG. 14.

In some implementations, the positioning apparatus 1360 is designed like the positioning apparatus 1460 of FIGS. 14 and 15. Each axial holder 1465*i*, 1465*ii*, 1465*iii* is configured to receive a respective stick 1405*i*, 1405*ii*, 1405*iii*. Moreover, each axial holder 1465*i*, 1465*ii*, 1465*iii* is defined by a pair of respective first and second gripping apparatuses (1400*i*A, 1400*i*B), (1400*ii*A, 1400*ii*B), and (1400*iii*A, 1400*iii*B). For example, the axial holder 1465*i* is defined by a portion of the first gripping apparatus 1400*i*A and the second gripping apparatus 1400*i*B; the axial holder 1465*ii* is defined by a portion of the first gripping apparatus 1400*ii*A and the second gripping apparatus 1400*ii*B; and the axial holder 1465*iii* is defined by a portion of the first gripping apparatus 1400*iii*A and the second gripping apparatus 1400*iii*B. While three axial holders 1465*i*, 1465*ii*, 1465*iii* are shown in this implementation, it is possible for the positioning apparatus 1460 to have more than or fewer than three axial holders.

The distance d between the sticks 1305*i*, 1305*ii*, 1305*iii* is determined depending on the application or the use of the sticks 1305*i*, 1305*ii*, 1305*iii* and also is configured to provide for independent thermal control of the sticks 1305*i*, 1305*ii*, 1305*iii*. This means that the distance d (relative to the extent or diameter of each stick) is great enough to enable independent thermal control of each stick. When one stick is being controlled, the axial holder 1365 associated with that stick includes a phase change material that is heated or cooled. The distance d is great enough so that the heating or cooling of the phase change material of one axial holder (associated with a particular stick) is thermally insulated or independent from the phase change material(s) of another axial holder associated with another stick. Indeed, the distance d is large enough to ensure thermal insulation between the sticks to enable heating of the phase change material(s) associated with a plurality of sticks that are adjacent to a particular stick in which the phase change material(s) of that particular stick is kept at a relatively cooler temperature. The distance d can depend on other factors such as a size or volume of the phase change material or an application of use for the positioning apparatus 1360. To the extent that heat flows between the phase change materials of each axial holder or if each axial holder begins at a different temperature at a beginning of a cycle, the heating amplitudes and durations of heating can be adjusted such that all of the phase change material that is intended to melt does so at the same time and any excess heat reaching those not intended to melt is reduced or minimized.

For example, d can be on the order of a few times the size or extent (for example, a diameter) of the sticks. The distance d can be 3-6 times the value of the diameter of the sticks. Thus, if the diameter of each of the sticks is about 100 μm, then the distanced between the sticks can be about 250-1000 μm.

The first gripping apparatus 1400*i*A is configured to interact with (grip and release) a first region of the stick 1405*i* and the second gripping apparatus 1400*i*B is configured to interact with (grip and release) a second region of the stick 1405*i*. The first gripping apparatus 1400*ii*A is configured to interact with (grip and release) a first region of the stick 1405*ii* and the second gripping apparatus 1400*ii*B is configured to interact with (grip and release) a second region of the stick 1405*ii*. Lastly, the first gripping apparatus 1400*iii*A is configured to interact with (grip and release) a first region of the stick 1405*iii* and the second gripping apparatus 1400*iii*B is configured to interact with (grip and release) a second region of the stick 1405*iii*.

Additionally, each axial holder 1465*i*, 1465*ii*, 1465*iii* is fixed to the actuator drive 1442 by fixing each of the respective first gripping apparatuses 1400*i*A, 1400*ii*A, 1400*iii*A and each of the second gripping apparatuses 1400*i*B, 1400*ii*B, 1400*iii*B to the actuator drive 1442. One way to accomplish this is to arrange the first gripping apparatuses 1400*i*A, 1400*ii*A, 1400*iii*A on a shared first substrate 1420A and to arrange the second gripping apparatuses 1400*i*B, 1400*ii*B, 1400*iii*B on a shared second substrate 1420B. In this way, the axial holders 1465*i*, 1465*ii*, 1465*iii* are fixed to the actuator drive 1442 by way of a shared fixing mechanism 1466 that includes both the first substrate 1420A and the second substrate 1420B. The first substrate 1420A is fixed to the first end 1442_1 of the actuator drive 1442 and the second substrate 1420B is fixed to the second end 1442_2 of the actuator drive 1442.

The gripping apparatuses (1400*i*A, 1400*i*B) associated with the axial holder 1465*i* are aligned with each other along the axial direction which is parallel with the z axis. In this way, the stick 1405*i* that is received in the axial holder 1465*i* is free to translate along the z axis with minimal forces applied in the directions perpendicular to the z axis. Similarly, the gripping apparatuses (1400*ii*A, 1400*ii*B) associated with the axial holder 1465*ii* are aligned with each other along the axial direction which is parallel with the z axis. In this way, the stick 1405*i* that is received in the axial holder 1465*ii* is free to translate along the z axis with minimal forces applied in the directions perpendicular to the z axis. Lastly, the gripping apparatuses (1400*iii*A, 1400*iii*B) associated with the axial holder 1465*iii* are aligned with each other along the axial direction which is parallel with the z axis. In this way, the stick 1405*iii* that is received in the axial holder 1465*iii* is free to translate along the z axis with minimal forces applied in the directions perpendicular to the z axis.

Each of the first gripping apparatuses 1400*i*A, 1400*ii*A, 1400*iii*A is designed similarly to the first gripping apparatus 800A in that it contains a first phase change material such as 825A that is configured to receive a first region of the respective stick 1405*i*, 1405*ii*, 1405*iii* and also a first temperature adjusting device such as 815A that is received in the first substrate 1420A. Each first temperature adjusting device in each first gripping apparatus 1400*i*A, 1400*ii*A, 1400*iii*A is in communication with a sub-controller 1430A, which is in communication with the controller 1445. The first phase change material is thermally coupled with the first temperature adjusting device such that a temperature change in the first temperature adjusting device causes a temperature change in the first phase change material.

Each of the second gripping apparatuses 1400*i*B, 1400*ii*B, 1400*iii*B is designed similarly to the second gripping apparatus 800B in that it contains a second phase change material such as 825B that is configured to receive a second region of the respective stick 1405*i*, 1405*ii*, 1405*iii* and also a second temperature adjusting device such as 815B that is received in the second substrate 1420B. Each second temperature adjusting device in each second gripping apparatus 1400*i*B, 1400*ii*B, 1400*iii*B is in communication with a sub-controller 1430B, which is in communication with the controller 1445. The second phase change material is thermally coupled with the second temperature adjusting device such that a temperature change in the second temperature adjusting device causes a temperature change in the second phase change material.

The controller 1445 (by way of the sub-controller 1431) provides the actuation signal to the single actuator drive 1442. For example, the actuation signal can be temporally-varying like the signal 1032 (with reference to FIG. 10B). This temporally-varying signal 1032 controls an axial position associated with the single actuator drive 1442.

Additionally, the controller 1445 can provide an independent signal (or signals) to each of the axial holders 1465*i*, 1465*ii*, 1465*iii*. This can be accomplished by sending a first signal to the first gripping apparatus 1400*i*A, 1400*ii*A, or 1400*iii*A via the sub-controller 1430A and sending a second signal to the second gripping apparatus 1400*i*B, 1400*ii*B, or 1400*iii*B via the sub-controller 1430B. In particular, the independent signal that is provided to a gripping apparatus is actually provided to the temperature adjusting device associated with that gripping apparatus, and the state of a particular phase change material is selected by adjustment of the provided independent signal to the temperature adjusting device thermally coupled with the phase change material.

In operation, the positioning apparatus 1360 (and 1460) is used to independently control the position of each stick 1305*i*, 1305*ii*, 1305*iii* along its respective axial direction and using only a single actuator drive 1342. FIGS. 16A-16E show examples of various configurations of the sticks 1305*i*, 1305*ii*, 1305*iii*. The sticks 1305*i*, 1305*ii*, 1305*iii* are positioned relative to an element 1670. As discussed above, the sticks 1305*i*, 1305*ii*, 1305*iii* can be used as actuators to effect or modify one or more characteristics of the element 1670. For example, each stick 1305*i*, 1305*ii*, 1305*iii* can include an electrical conductor (such as a cable or wire); a measurement probe; a capillary tube; an optical waveguide; an optical fiber; a carbon fiber or filament; or a sonic waveguide. If the stick 1305*i*, 1305*ii*, 1305*iii* is a measurement probe, then it could include an electrical testing probe, a silicon probe, an electrical recording probe, or an ultrasonic probe. In some implementations, one or more of the sticks 1305*i*, 1305*ii*, 1305*iii* can be of a first type (such as an electrical conductor (such as a cable or wire)) while one of the sticks can be of a second type (such as a measurement probe; a capillary tube; an optical waveguide; an optical fiber; a carbon fiber or filament; or a sonic waveguide). Thus, it is possible for a particular positioning apparatus 1360, 1460 to include sticks of different types.

For example, in FIG. 16A, each of the sticks 1305*i*, 1305*ii*, 1305*iii* is at the same axial position (along the z direction) relative to the element 1670 and in this case the sticks 1305*i*, 1305*ii*, 1305*iii* are all separated from the element 1670. In FIG. 16B, each of the sticks 1305*i*, 1305*ii*, 1305*iii* is at the same axial position relative to the element 1670 and in this case, the sticks 1305*i*, 1305*ii*, 1305*iii* are interacting with the element 1670 at a first interacting axial position. In FIG. 16C, sticks 1305*i*, 1305*ii* are interacting with the element 1670 at the first interacting axial position and the stick 1305*iii* is interacting with the element 1670 at a second interacting axial position. In FIG. 16D, the stick 1305*i* is interacting with the element 1670 at the first interacting axial position and the sticks 1305*ii*, 1305*iii* are interacting with the element 1670 at the second interacting axial position. In FIG. 16E, the sticks 1305*i*, 1305*iii* are separated from the element 1670 at the same axial position and the stick 1305*ii* is interacting with the element 1670 at the first interacting axial position.

Figure 17A:
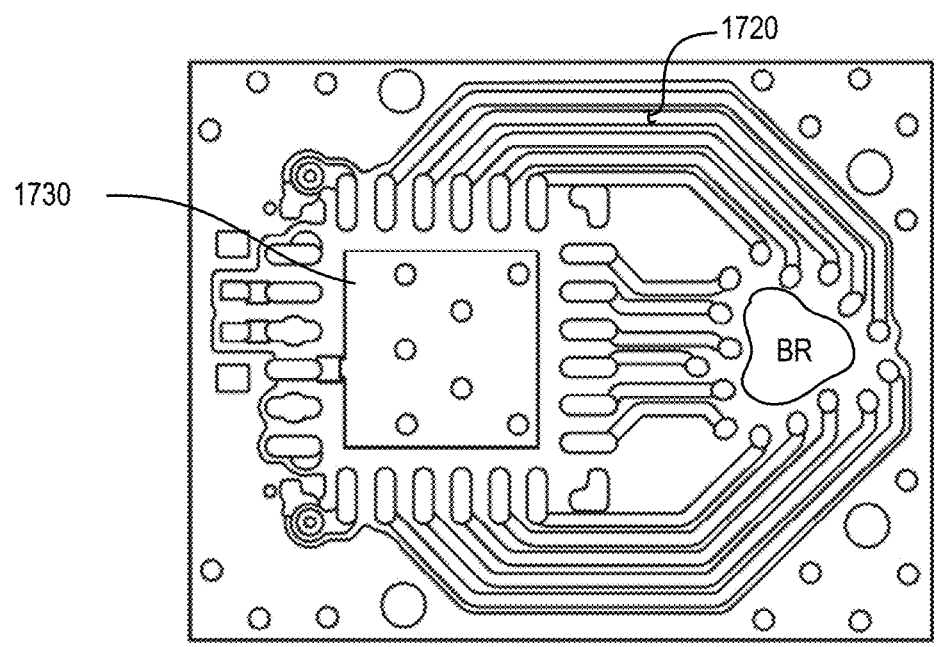
FIGS. 17A-17D show top plan views of an implementation of a positioning apparatus such as the positioning apparatus shown in FIGS. 13-15, with steps in manufacturing depicted.

FIGS. 17A-17D show implementations of the placement and geometry of axial holders (such as 1400*i*A, 1400*ii*A, 1400*iii*A) on a first substrate (such as the first substrate 1420A) to be used in a positioning apparatus (such as the positioning apparatus 1460). In FIG. 17A, a substrate 1720 such as a printed circuit board or PCB includes a blank region BR (such as the substrate 120 shown in FIG. 7A). Also shown in FIG. 17A is a controller 1730.

Figure 17B:
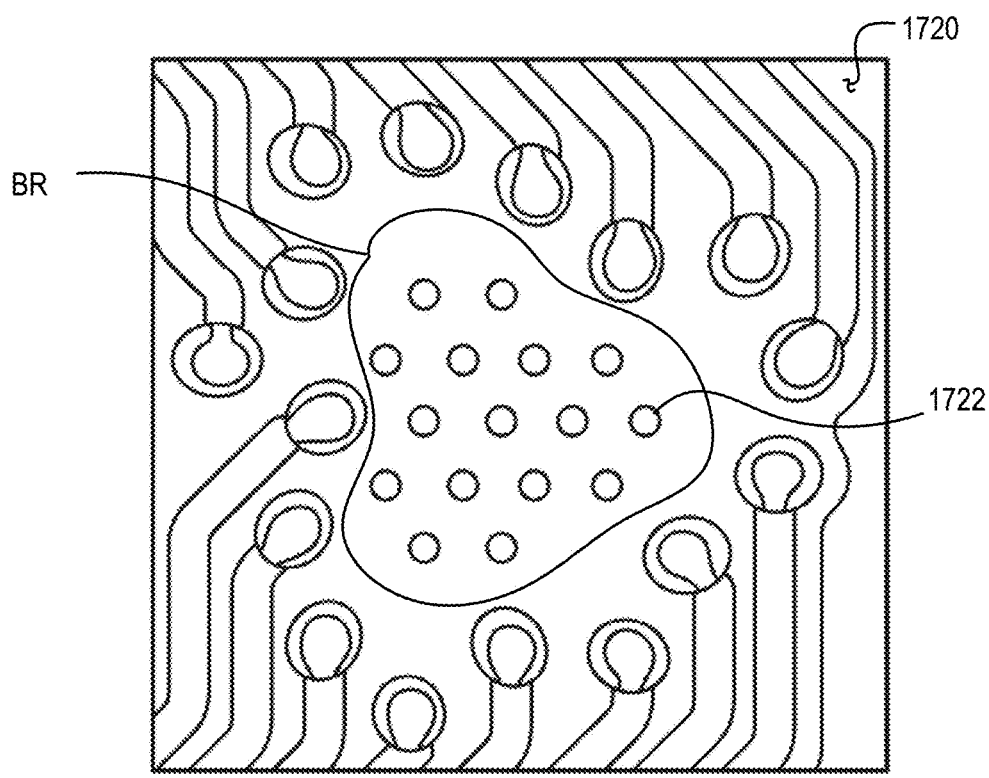

In FIG. 17B, sixteen open regions 1722 are have been formed, each open region 1722 having a circular cross section and being placed within the previously blank region BR of the substrate 1720. This is similar to the formation of the open region 122 in the substrate 120 of FIG. 7B. For example, the open regions 1722 can be holes drilled into the blank region BR. The PCB can include thermally-conductive and sinking metal planes slightly separated from the open regions 1722 to facilitate heat transfer away from the open regions 1722 in use.

Figure 17C:
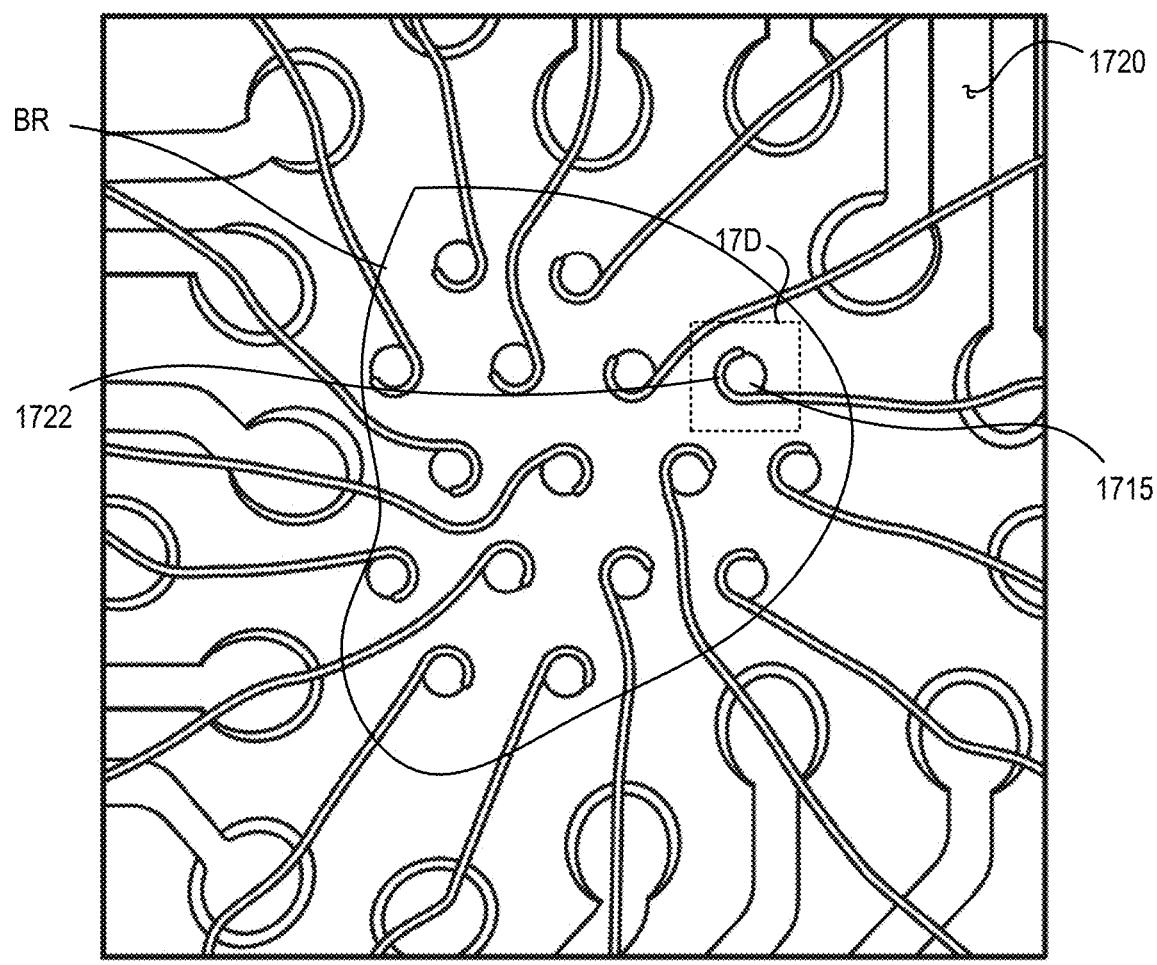
Figure 17D:
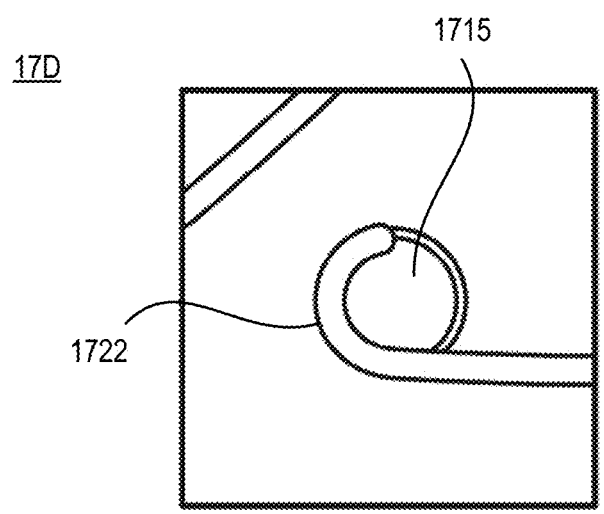

In FIG. 17C, sixteen temperature adjusting devices 1715 are formed to be held within the substrate 1720 (for example, in each of the open regions 1722). For example, the temperature adjusting devices 1715 can be a resistive material epoxied into each open region 1722, which can be soldered at FIG. 17D. This is similar to the step shown in FIG. 7C. A close-up of one of the temperature adjusting devices 1715 and open regions 1722 is shown in FIG. 17D.

Figure 18A:
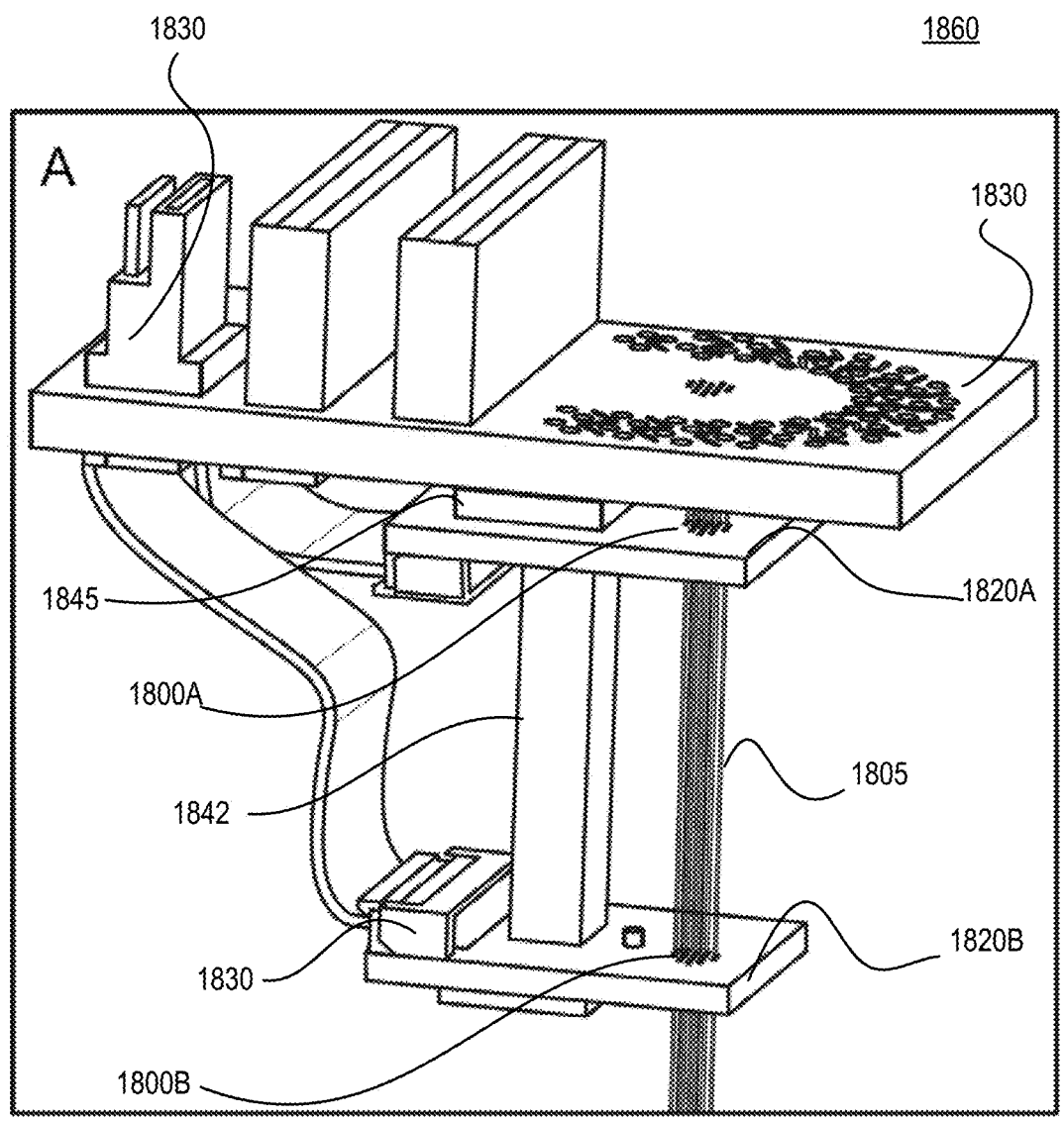
FIGS. 18A, 18B, and 18D show perspective views of an implementation of a positioning apparatus such as the positioning apparatus of FIGS. 13-15.
Figure 18B:
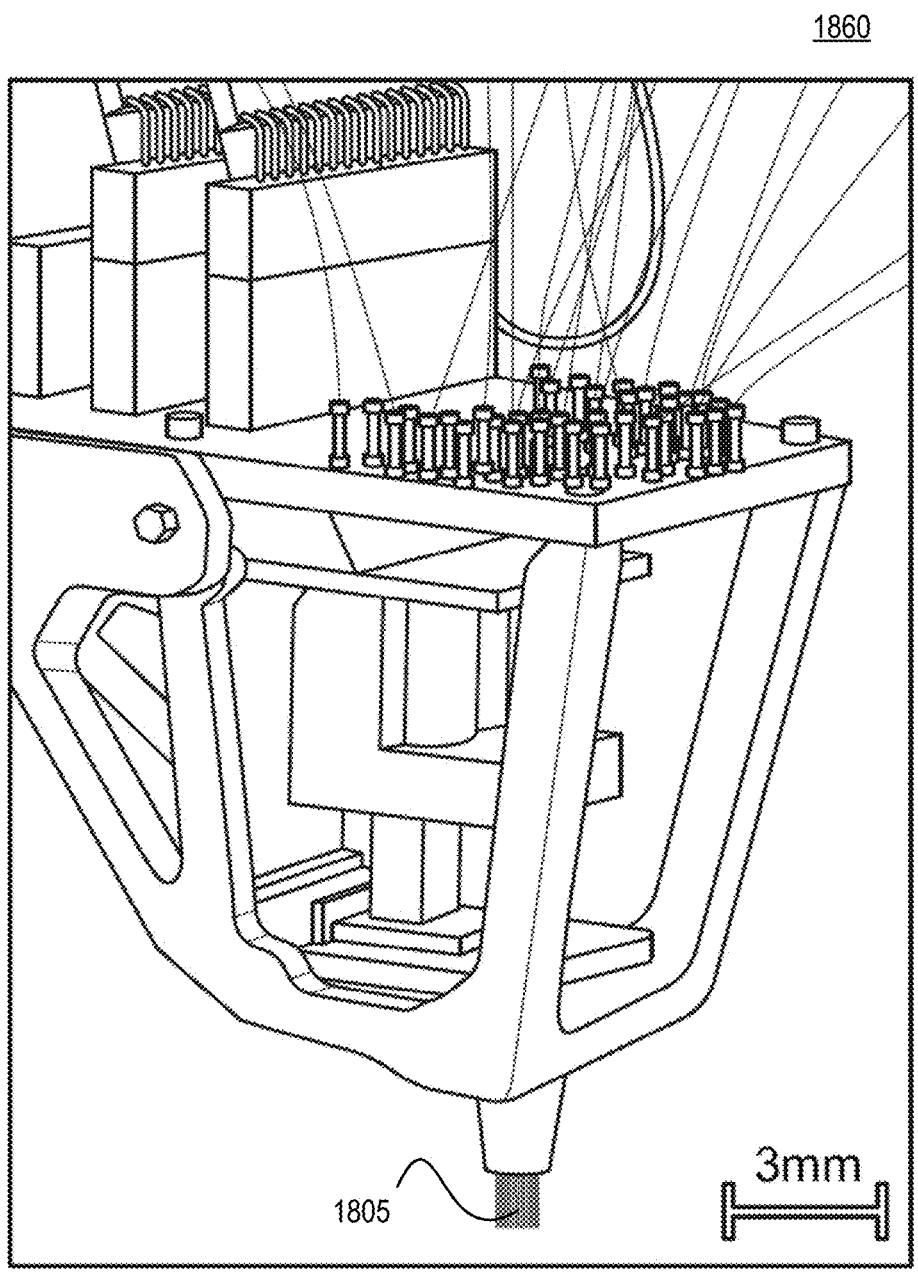
Figure 18E:
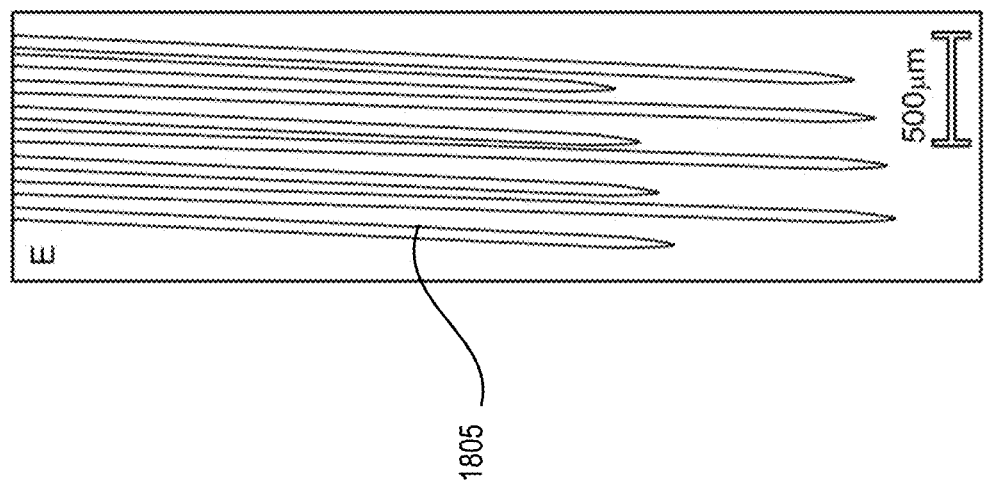
FIGS. 18C and 18E show an implementation of the sticks of the positioning apparatus of FIGS. 13-15.
Figure 18C:
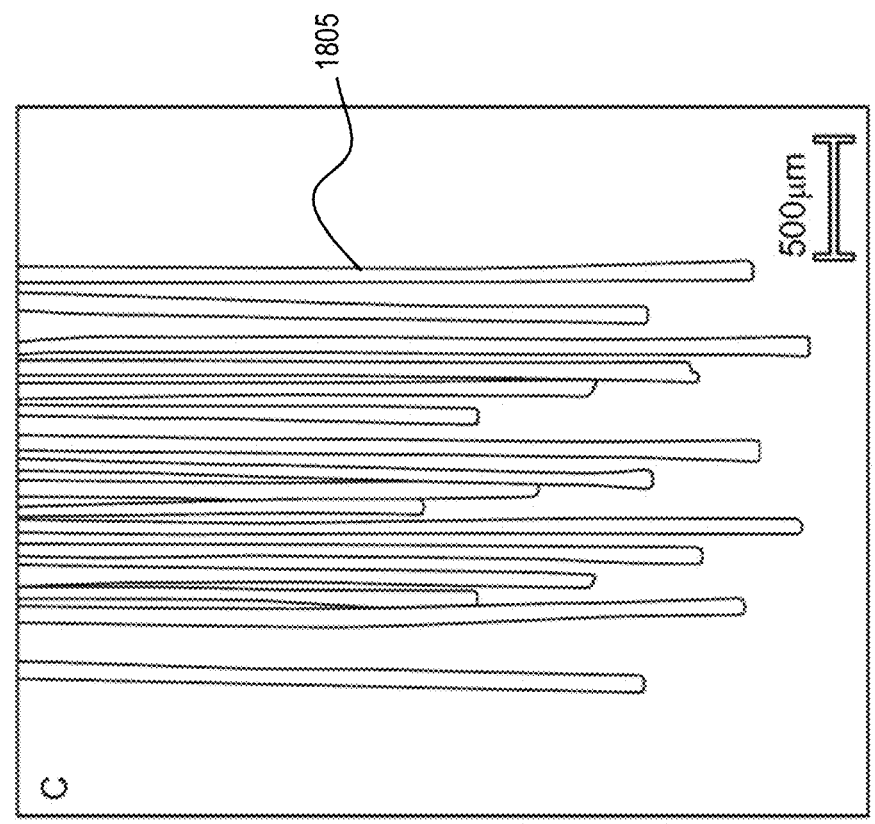
Figure 18D:
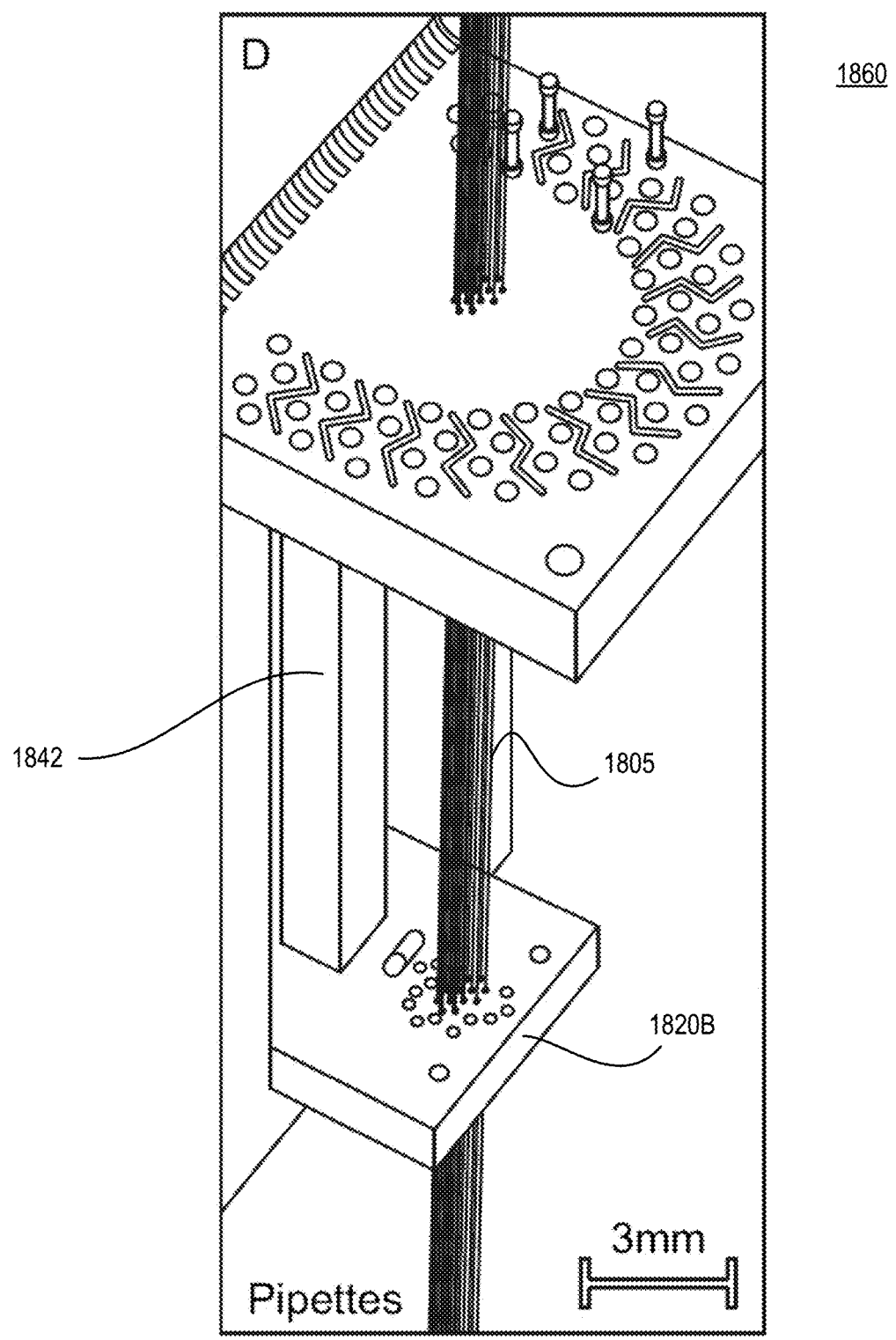

FIGS. 18A, 18B, and 18D show perspective views of a positioning apparatus 1860 designed like the positioning apparatus 1360 of FIG. 13 and the positioning apparatus 1460 of FIG. 14. The positioning apparatus 1860 includes a set of axial holders configured to receive a respective stick 1805 (collectively designated as 1805 in FIG. 18A, 18B, 18D). Each axial holder is defined by a pair of respective first and second gripping apparatuses (collectively designated as 1800A, 1800B. For example, each axial holder is defined by a portion of the first gripping apparatus 1800A and the second gripping apparatus 1800B. Each of the first gripping apparatuses 1800A is formed on a shared substrate 1820A and each of the second gripping apparatuses 1800B is formed on a shared substrate 1820B.

The positioning apparatus 1860 is designed to independently translate each stick of the plurality of sticks 1805 along an axial direction of that stick using a single actuator drive 1842 movable along its own axial direction, which is parallel with the z axis, and under control of a controller 1845, as discussed above. The controller 1845 is in communication with the single actuator drive 1842, and with the plurality of axial holders via a sub-controller that includes components 1830.

FIGS. 18C and 18E show the sticks 1805 that are positionable with the positioning apparatus 1860.

Figure 19A:
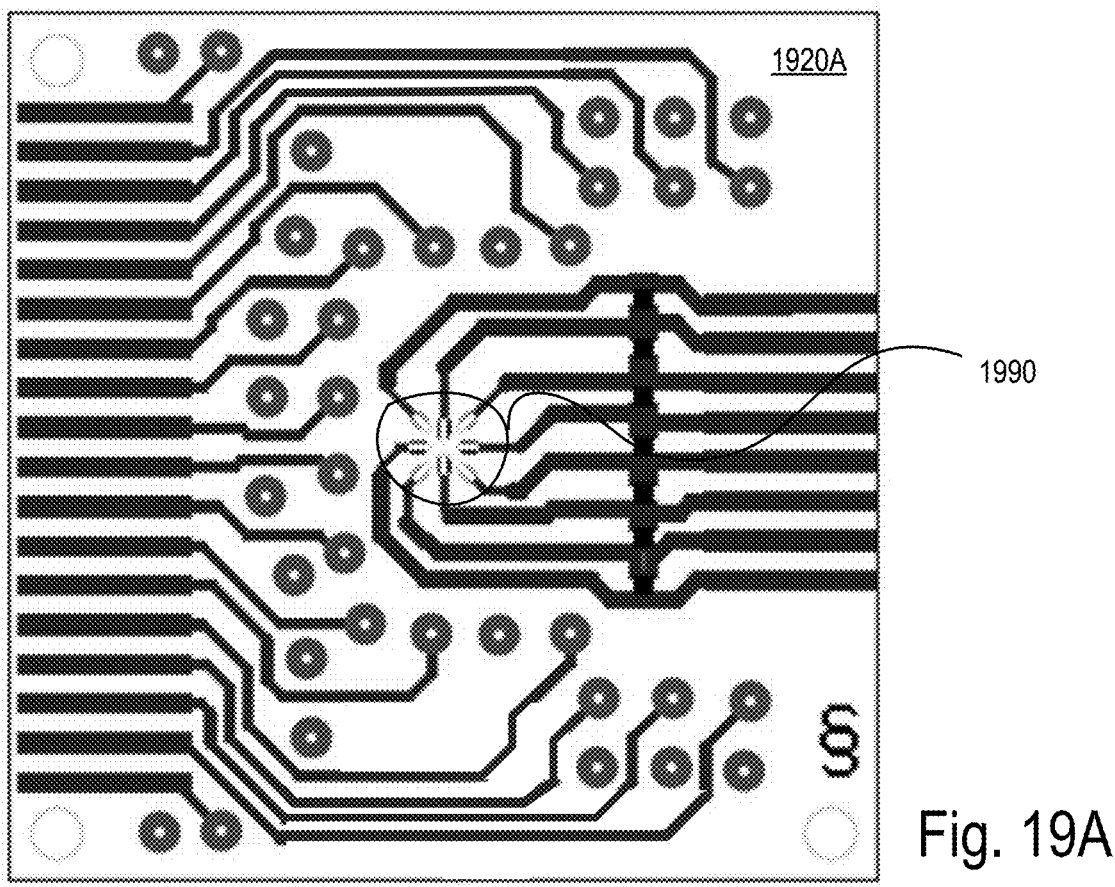
FIG. 19A shows a schematic representation of an implementation of a positioning apparatus of FIGS. 13-15.
Figure 19B:
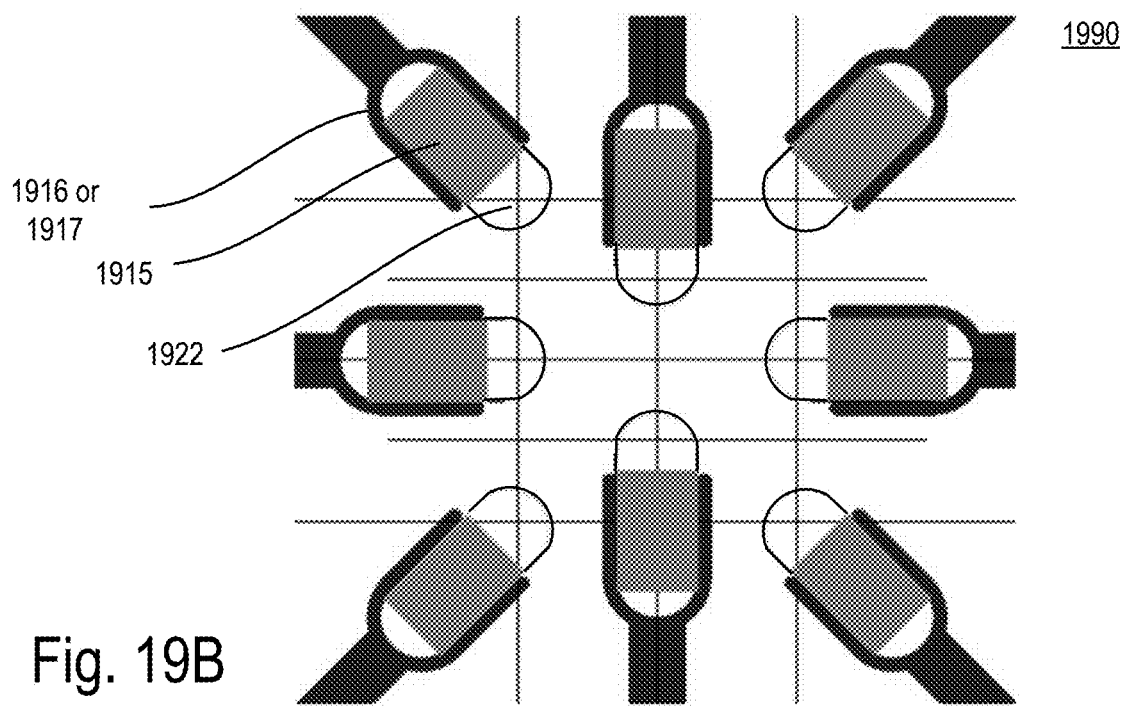
FIG. 19B shows a close-up view of an area of a substrate of the positioning apparatus of FIG. 19A in which each temperature adjusting device is a chip resistor.

FIG. 19A shows a schematic of the placement and geometry of axial holders (such as 1400*i*A, 1400*ii*A, 1400*iii*A) on a first substrate (such as the first substrate 1420A) to be used in a positioning apparatus (such as the positioning apparatus 1460). In FIG. 19A, eight axial holders are shaped with a circular cross section and are within an area 1990A of substrate 1920A and details of the area 1900A are shown in FIG. 19B. The design of the axial holders in area 1990A uses a chip resistor 1915 embedded within an open region 1922 that receives a phase change material. This is similar to the design shown in FIGS. 5A and 5B. The chip resistor 1915 is controlled by a controller (such as controller 130), which includes the power source that supplies the current to the chip resistor 1915 by way of electrically conductive elements 1916, 1917.

In some implementations the gripping apparatus 100 is a stick gripper including a stick such as a probe. The stick gripper includes an electrically-connected resistive via (as a temperature adjusting device) in a board (such as a printed circuit board) filled with a phase change material 125 (for example, a wax or paraffin). When no current from a power supply flows through the resistive via, the phase change material 125 in the via is in a solid state and the probe in the via is gripped. When the current flows through the resistive via, the phase change material 125 in the via changes to the liquid state (melts) and the probe in the via is released. The phase change material 125 in the liquid state remains in the via due at least in part to the capillary action. The grip and release action of the gripper is controlled electronically. The resistive via can be made of a plated or deposited resistive material in the board via, chip resistor adjacent to the board via, wire-wound resistor in the board via, or carbon paste coated in the board via.

In other implementations, a positioning apparatus (such as the apparatus 840 or the apparatus 1360) is based on the gripping apparatus 100 that is capable of independently moving multiple probes along one axis using a single mechanical (for example, screw based drive), electrical (for example, piezoelectric actuator or stepper motor), or thermal (for example, shape memory alloy) positioner. The positioning apparatus includes two parallel substrates (or boards such as printed circuit boards) with a single (such as the apparatus 840) or an array of resistive vias aligned along one axis (such as the apparatus 1360). One board is fixed/immobile while another board is movable/mobile by a positioner/actuator (the actuator drive 842 or 1342). By electronically controlling the current though the aligned vias (and therefore the grip or release of the probes in the vias) in the respective top and bottom boards, each probe held in the device can be independently translated in either direction (up or down or fixed in position) with a single mechanical or electronic actuator. The probes in the board vias moved by the device can be of any shape, as the liquid phase change material in the board via that grips the probe conforms to the probe shape.

Examples of the stick 105, 805, 1305*i, ii, iii* include electrical testing probes, optical fibers, silicon probes, glass pipette/capillary, carbon fibers, electrical recording probes, and ultrasonic probes. The positioning apparatus and gripping apparatus can be constructed from non-ferrous parts and therefore can be made MRI compatible. The wire electrodes and glass capillary pipette electrodes for neural cell electrical spike detection, and applications in which one or multiple closely spaced probes need to be translated, positioned, or targeted with high precision are envisioned with this probe gripper principle and positioner device.

The choice of the phase change material in the board vias can be made so that the device is operational at different operating temperatures (low temperature operation, room temperature operation, physiological temperature operation, high temperature operation).

The gripping apparatus 100, the positioning apparatus 840, and the positioning apparatus 1360 have the following benefits. For example, a plurality of probes can be independently positioned with single positioner/actuator, such as, for example, shown in FIG. 13, and because of this size, cost, and complexity can be reduced while density can be increased relative to prior designs.

Each gripping apparatus 100 (which includes the phase change material 125, the temperature adjusting device 115, and the substrate 120 can be made small and has a simple design, and many of these gripping apparatuses can be packed next to each other to form a positioning apparatus such as the positioning apparatus 860. For example, micronscale independent positioning of each stick 1305*i*, 1305*ii*, 1305*iii* in the positioning apparatus 1360 can be obtained with an electric/motorized actuator drive 1342 (which can be a positioner such as, for example, a piezoelectric actuator). Accordingly, there is potential for significant miniaturization and weight reduction.

The phase change material 125 remains in the open region 122 of the substrate 120 at least in part due to capillary action.

Any of the apparatuses (gripping apparatus 100, positioning apparatus 840, and positioning apparatus 1360) can be made to be fully electronically operational which allows remote control and automation of the apparatuses.

Technology that is implemented on a substrate 120 that is a printed circuit board is well-developed and inexpensive.

The gripping apparatus 100 can be designed to interact with a stick 105 of different shapes or application. For example, the stick 105 or one or more of the sticks used in the positioning apparatus 1360 can be an electrical probe, a silicon probe, a glass pipette, a carbon or optical fiber, an ultrasonic probe. In general, any stick 105 that is stiff enough to be grabbed by the phase change material 125 can be used.

The gripping apparatus 100, positioning apparatus 840, and positioning apparatus 1360 can be made of non-ferrous components, which potentially make these apparatuses compatible with magnetic resonance imaging machines. Additionally, the choice of phase change material 125 in the apparatuses allows for operation at different temperatures chosen based on the application.

The gripping apparatus 100, and the positioning apparatuses 840, 1360 find applications in neuroscience where independent positioning of many probes in the brain is desired. Multiple probes can be independently positioned with single translator (actuator drive) as opposed to plural translators. Simplicity, miniature gripper size, low cost, low weight, high positioning precision, variety of probes that can be gripped and translated, and fully electronic operation add to the valuable features of the gripping apparatus 100 and the positioning apparatuses 840, 1360.

What is claimed is:

1. A gripping apparatus comprising:
a temperature adjusting device held in a substrate wherein the substrate defines an open region;
a phase change material held within the open region and thermally coupled with the temperature adjusting device such that a temperature change in the temperature adjusting device causes a temperature change in the phase change material; and
a controller connected to the temperature adjusting device and configured to send a signal to the temperature adjusting device to change its temperature and thereby change the temperature of the phase change material that is thermally coupled with the temperature adjusting device;
wherein:
when the phase change material is at a temperature below a first transition temperature, the phase change material is in a solid state and the phase change material is configured to grip a stick within the phase change material; and when the phase change material is at a temperature above a second transition temperature, the phase change material is in a liquid state and the phase change material is configured to loosen its grip on the stick such that the stick is capable of moving through the phase change material.

2. The gripping apparatus of claim 1, wherein the stick extends through the phase change material.

3. The gripping apparatus of claim 1, wherein the phase change material includes one or more of: wax; paraffin wax; and alkane hydrocarbon.

4. The gripping apparatus of claim 3, wherein the alkane hydrocarbon includes one or more of: n-octacosane, n-heptacosane, n-hexacosane, n-pentacosane, n-tetracosane, n-docosane, n-tricosane, n-heneicosane, n-eicosane, n-nonadecane, n-octadecane, n-heptadecane, n-hexadecane, n-pentadecane, n-tetradecane, and n-tridecane.

5. The gripping apparatus of claim 1, wherein the phase change material is selected so that the transition between the solid state and the liquid state at the first or second transition temperature occurs at an operating temperature for the gripping apparatus.

6. The gripping apparatus of claim 1, wherein the stick is rigid enough to withstand motion through the phase change material without fracturing or bending or kinking.

7. The gripping apparatus of claim 1, wherein the first transition temperature and the second transition temperature are at room temperature, at a temperature of a living organism, at a temperature below room temperature, or at a temperature above room temperature.

8. The gripping apparatus of claim 1, wherein the stick includes one or more of: at least one conductor; at least one measurement probe; at least one capillary tube; at least one optical waveguide; and at least one carbon fiber; and at least one sonic waveguide.

9. The gripping apparatus of claim 8, wherein the at least one measurement probe includes an electrical testing probe, a silicon probe, an electrical recording probe, or an ultrasonic probe.

10. The gripping apparatus of claim 1, wherein the substrate is generally defined in an x-y plane, and when the phase change material is at a temperature above the second transition temperature, the stick is capable of moving through the phase change material along a z axis that is perpendicular to the x-y plane.

11. The gripping apparatus of claim 1, wherein a cross section of the stick taken along a plane is a circular shape, a polygonal shape, or an irregular asymmetric shape.

12. The gripping apparatus of claim 1, wherein the temperature adjusting device comprises a resistive conductive wire and the controller includes a power source that supplies a current to the resistive conductive wire, wherein the resistive conductive wire changes its temperature as the current is changed.

13. The gripping apparatus of claim 1, wherein the temperature adjusting device comprises one or more of: a resistive material deposited in the open region of the substrate; a chip resistor adjacent to the open region of the substrate; a wire-wound resistor in the open region of the substrate; and a carbon paste coated in the open region of the substrate.

14. The gripping apparatus of claim 1, wherein the substrate includes a printed circuit board.

15. The gripping apparatus of claim 1, wherein the phase change material is held within the open region by way of capillary forces.

16. The gripping apparatus of claim 1, wherein the phase change material remains within the open region even if it is in the liquid state.

17. The gripping apparatus of claim 1, wherein the first transition temperature is equal to the second transition temperature.

18. A positioning apparatus comprising:
a single actuator drive movable along an axial direction;
a plurality of axial holders, each axial holder configured to receive a stick and each axial holder being fixed to the single actuator drive; and
a controller in communication with the single actuator drive and with the plurality of axial holders, and configured to:
provide an actuation signal to the single actuator drive; and
provide at least one independent signal to each of the axial holders;
whereby the position of each stick is independently adjustable along the axial direction by the adjustment of the provided at least one independent signal to each of the axial holders without adjusting the provided actuation signal to the single actuator drive.

19. The positioning apparatus of claim 18, wherein:
the single actuator drive includes a first end and a second end; and
the first and second ends are movable relative to each other along the axial direction.

20. The positioning apparatus of claim 19, wherein:
each axial holder includes a first gripping apparatus fixed to the first end of the single actuator drive and a second gripping apparatus fixed to the second end of the single actuator drive;
the second gripping apparatus is aligned along an axial direction with the first gripping apparatus; and
for each axial holder:
the first gripping apparatus is configured to receive a first region of the stick that is received in that axial holder and the second gripping apparatus is configured to receive a second region of the stick that is received in that axial holder.

21. The positioning apparatus of claim 20, wherein, for each axial holder:
the first gripping apparatus includes a phase change material that is configured to receive the first region of the stick that is received in that axial holder; and
the second gripping apparatus includes a phase change material that is configured to receive the second region of the stick that is received in that axial holder.

22. The positioning apparatus of claim 18, wherein:
providing the actuation signal to the single actuator drive comprises providing a temporally-varying signal to the single actuator drive, the temporally-varying signal controlling an axial position associated with the single actuator drive.

23. The positioning apparatus of claim 18, wherein:
each axial holder is configured to interact with at least two interaction regions of its associated stick;
at each interaction region, the stick is received in a gripping apparatus; and
providing at least one independent signal to each of the axial holders comprises providing an independent signal to each gripping apparatus in each axial holder.

24. The positioning apparatus of claim 23, wherein each gripping apparatus comprises:
a temperature adjusting device; and a phase change material thermally coupled with the temperature adjusting device such that a temperature change in the temperature adjusting device causes a temperature change in the phase change material;

wherein providing the independent signal to a gripping apparatus comprises providing an independent signal to the temperature adjusting device, and the state of the phase change material is selected by adjustment of the provided independent signal to the temperature adjusting device thermally coupled with the phase change material.

25. A method comprising:

providing a single actuation signal to a single actuator drive, wherein the single actuation signal controls a movement of the single actuator drive along an axial direction;

providing an independent signal to each axial holder of a plurality of axial holders, wherein each axial holder receives a stick and each axial holder is fixed to the single actuator drive; and independently adjusting a position of a stick along the axial direction by adjusting the provided independent signal to the axial holder that receives that stick and without adjusting the provided actuation signal to the single actuator drive.

26. The method of claim 25, wherein providing the single actuation signal to the single actuator drive comprises controlling a relative movement between a first end of the single actuator drive and a second end of the single actuator drive along the axial direction.

27. The method of claim 25, wherein providing the single actuation signal to the single actuator drive comprises providing a temporally-varying signal to the single actuator drive, the temporally-varying signal controlling an axial position associated with the single actuator drive.

28. The method of claim 25, wherein providing an independent signal to an axial holder comprises providing an independent signal to a gripping apparatus in that axial holder.

29. The method of claim 28, wherein providing the independent signal to a gripping apparatus comprises providing an independent signal to a temperature adjusting device of the gripping apparatus; further comprising selecting a state of a phase change material thermally coupled to the temperature adjusting device by adjusting the provided independent signal to the temperature adjusting device thermally coupled with that phase change material.

* * * * *